US012622918B2

(12) United States Patent
Kelly et al.

(10) Patent No.: US 12,622,918 B2
(45) Date of Patent: May 12, 2026

(54) FORMULATIONS AND DOSAGES FOR ADMINISTERING A COMPOUND THAT INHIBITS MCL1 PROTEIN

(71) Applicant: Amgen Inc., Thousand Oaks, CA (US)

(72) Inventors: Ron C. Kelly, Westlake Village, CA (US); Michael T. Kennedy, Newbury Park, CA (US); Stevedat K. La, Moorpark, CA (US)

(73) Assignee: AMGEN INC., Thousand Oaks, CA (US)

( * ) Notice: Subject to any disclaimer, the term of this patent is extended or adjusted under 35 U.S.C. 154(b) by 972 days.

(21) Appl. No.: 17/629,824

(22) PCT Filed: Apr. 23, 2020

(86) PCT No.: PCT/US2020/029446
§ 371 (c)(1),
(2) Date: Jan. 25, 2022

(87) PCT Pub. No.: WO2021/021259
PCT Pub. Date: Feb. 4, 2021

(65) Prior Publication Data

US 2022/0257607 A1 Aug. 18, 2022

Related U.S. Application Data

(60) Provisional application No. 62/880,383, filed on Jul. 30, 2019.

(30) Foreign Application Priority Data

Nov. 10, 2019 (EP) .................................... 19208217

(51) Int. Cl.

| | |
|---|---|
| ***A61K 31/553*** | (2006.01) |
| ***A61K 45/06*** | (2006.01) |
| ***A61K 47/02*** | (2006.01) |
| ***A61K 47/18*** | (2017.01) |
| ***A61K 47/69*** | (2017.01) |
| ***A61P 35/00*** | (2006.01) |
| ***A61P 35/02*** | (2006.01) |

(52) U.S. Cl.
CPC ............ *A61K 31/553* (2013.01); *A61K 45/06* (2013.01); *A61K 47/02* (2013.01); *A61K 47/183* (2013.01); *A61K 47/6951* (2017.08); *A61P 35/00* (2018.01); *A61P 35/02* (2018.01)

(58) Field of Classification Search
CPC .......... A61P 35/00; A61P 35/02; A61K 45/06; A61K 31/553; A61K 47/6951; A61K 47/02; A61K 47/183
See application file for complete search history.

(56) References Cited

U.S. PATENT DOCUMENTS 9,562,061 B2 * 2/2017 Brown ................. C07D 498/00
10,100,063 B2 * 10/2018 Brown .................... A61P 35/02
2016/0068545 A1 3/2016 Brown
2019/0062428 A1 2/2019 Paterson
2019/0091229 A1 3/2019 Lichenstein

FOREIGN PATENT DOCUMENTS

WO 2016033486 3/2016

OTHER PUBLICATIONS

Akers, Michael J. "Excipient-drug interactions in parenteral formulations." Journal of pharmaceutical sciences 91, No. 11 (2002): 2283-2300 (Year: 2002).*

Strickley, Robert G. "Solubilizing excipients in oral and injectable formulations." Pharmaceutical research 21 (2004): 201-230 (Year: 2004).*

Tonog P, Lakhkar AD. Normal Saline. [Updated Oct. 16, 2022]. In: StatPearls [Internet]. Treasure Island (FL): StatPearls Publishing; Jan. 2025-. Available from: https://www.ncbi.nlm.nih.gov/books/NBK545210/ (Year: 2022).*

Saokham, P., Muankaew, C., Jansook, P. and Loftsson, T., 2018. Solubility of cyclodextrins and drug/cyclodextrin complexes. Molecules, 23(5), p. 1161) (Year: 2018).*

Ashkenazi, A., et al., "From basic apopotosis discoveries to advanced selective BCL-2 family inhibitors," Nature Reviews Drug Discovery, vol. 16, pp. 273-284 (2017).

Beroukhim, R., et al., "The landscape of somatic copy-number alteration across human cancers," Nature, vol. 463, pp. 899-905 (2010).

(Continued)

*Primary Examiner* — James H Alstrum-Acevedo
*Assistant Examiner* — Carolyn L. Ladd

(57) ABSTRACT

The present disclosure is drawn to pharmaceutical formulations, aqueous solutions, and methods of treating cancer using the disclosed pharmaceutical formulations and aqueous solutions. The formulations and solutions comprise compounds of Formula I and may further comprise a cyclodextrin compound, such as hydroxypropyl-β-cyclodextrin and a buffer, such as glycine. The methods of treating cancer include the treatment of hematological malignances such as acute myelogenous leukemia, multiple myeloma, and non-Hodgkin's lymphoma.

I

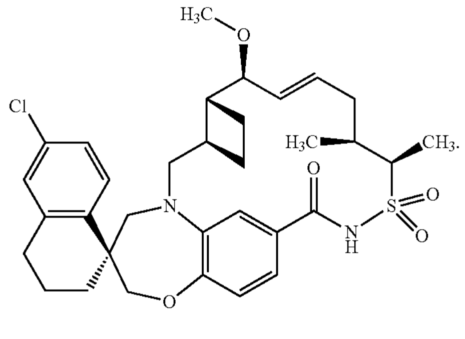

22 Claims, 8 Drawing Sheets

(56) References Cited

OTHER PUBLICATIONS

Caenepeel, S. et al., "AMG 176, a Selective MCL1 Inhibitor, Is Effective in Hematologic Cancer Models Alone and in Combination with Established Therapies," Cancer Discov., vol. 8(12), pp. 1582-1597 (2018).
Czabotar, P., et al. "Control of apoptosis by the BCL-2 protein family: implications for physiology and therapy.," Nat. Rev. Mol. Cell Biol., vol. 15, pp. 49-63 (2014).
Fouad, Y., et al., "Revisiting the hallmarks of cancer," Am. J. Cancer Res., vol. 7(5), pp. 1016-1036 (2017).
Glaser, S., et al., "Anti-apoptotic Mcl-1 is essential for the development and sustained growth of acute myeloid leukemia," Genes and Development, vol. 12, pp. 120-125 (2012).
Hanahan D., et al., "Hallmarks of cancer: the next generation," Cell, vol. 144(5), pp. 646-674 (2011).
Kotschy, A., et al., "The MCL1 inhibitor S63845 is tolerable and effective in diverse cancer models," Nature, vol. 538, pp. 477-482 (2016).
Kozopas, K., et al., "MCL1, a gene expressed in programmed myeloid cell differentiation, has sequence similarity to BCL2," Proc. Natl. Acad. Sci., vol. 90, pp. 3516-3520 (1993).
Merino, D., et al., "Synergistic action of the MCL-1 inhibitor S63845 with current therapies in preclinical models of triple-negative and HER2-amplified breast cancer," Sci. Trans. Med., vol. 9, pp. 1-10 (2017).
Strasser, A., et al., "Deciphering the rules of programmed cell death to improve therapy of cancer and other diseases," Embo J., vol. 30, pp. 3667-3683 (2011).
Thomas, R., et al., "Loss of MCL-1 leads to impaired autophagy and rapid development of heart failure," Genes & Dev., vol. 27, pp. 1365-1377 (2013).
Van Delft, M., et al., "The BH3 mimetic ABT-737 targets selective Bcl-2 proteins and efficiently induces apoptosis via Bak/Bax if Mcl-1 is neutralized," Cancer Cell, vol. 10, 389-399 (2006).
Wang, X., et al., "Deletion of MCL-1 causes lethal cardiac failure and mitochondrial dysfunction," Genes Dev., vol. 27, pp. 1351-1364 (2013).
Wertz, I., et al., "Sensitivity to antitubulin chemotherapeutics is regulated by MCL1 and FBW7," Nature, vol. 471, pp. 110-114 (2011).
Xiang, W., et al., "MCL-1 inhibition in cancer treatment," OncoTargets and Therapy, vol. 11, pp. 7301-7314 (2018).

* cited by examiner

ANOVA = analysis of variance; BAK = BCL2 homologous antagonist/killer; MCL1 = myeloid cell leukemia 1

Matrigel™ plugs were collected after a single treatment with AMG 176 and snap frozen for ex vivo luciferase analysis (n = 3). Luminescence represents the normalized group average of the raw signal. Data represent mean ± SE of the mean for each group.

FIG. 2

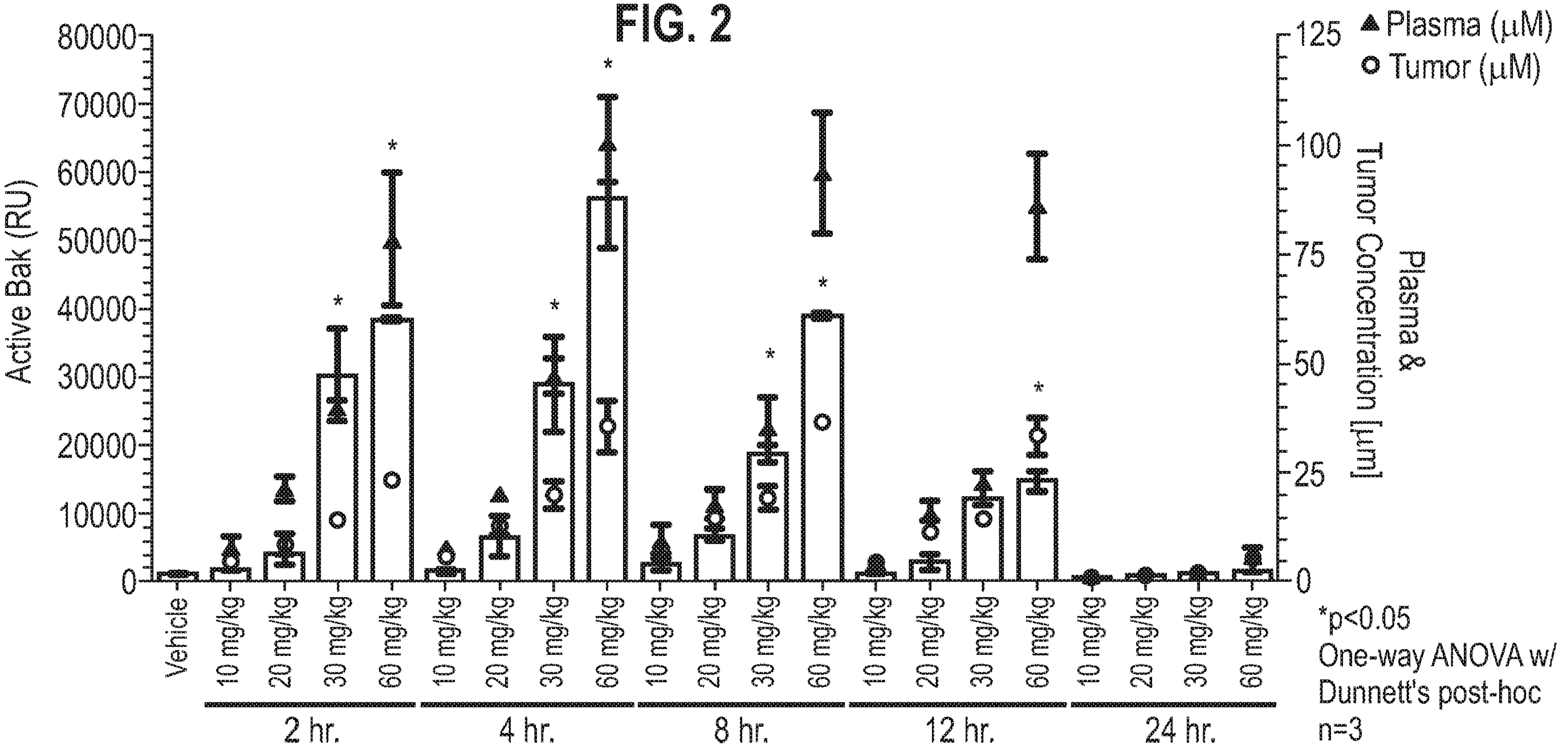

ANOVA = analysis of variance; BAK= BCL2 homologous antagonist/killer; OPM2-Luc = OPM2 cell stably transduced with the luciferase gene; RU = response unit Mice bearing OPM2-Luc tumors were treated with either vehicle or a single-dose of AMG 176. Tumors were harvested for BAK activation analysis (n = 3), measured by a Meso Scale Discovery Immunoassay. Data represent mean± SE of the mean of BAK activation for each group. Mean plasma and tumor concentrations of AMG 176 were determined at each time and dose, and are plotted on the right y-axis.

FIG. 3

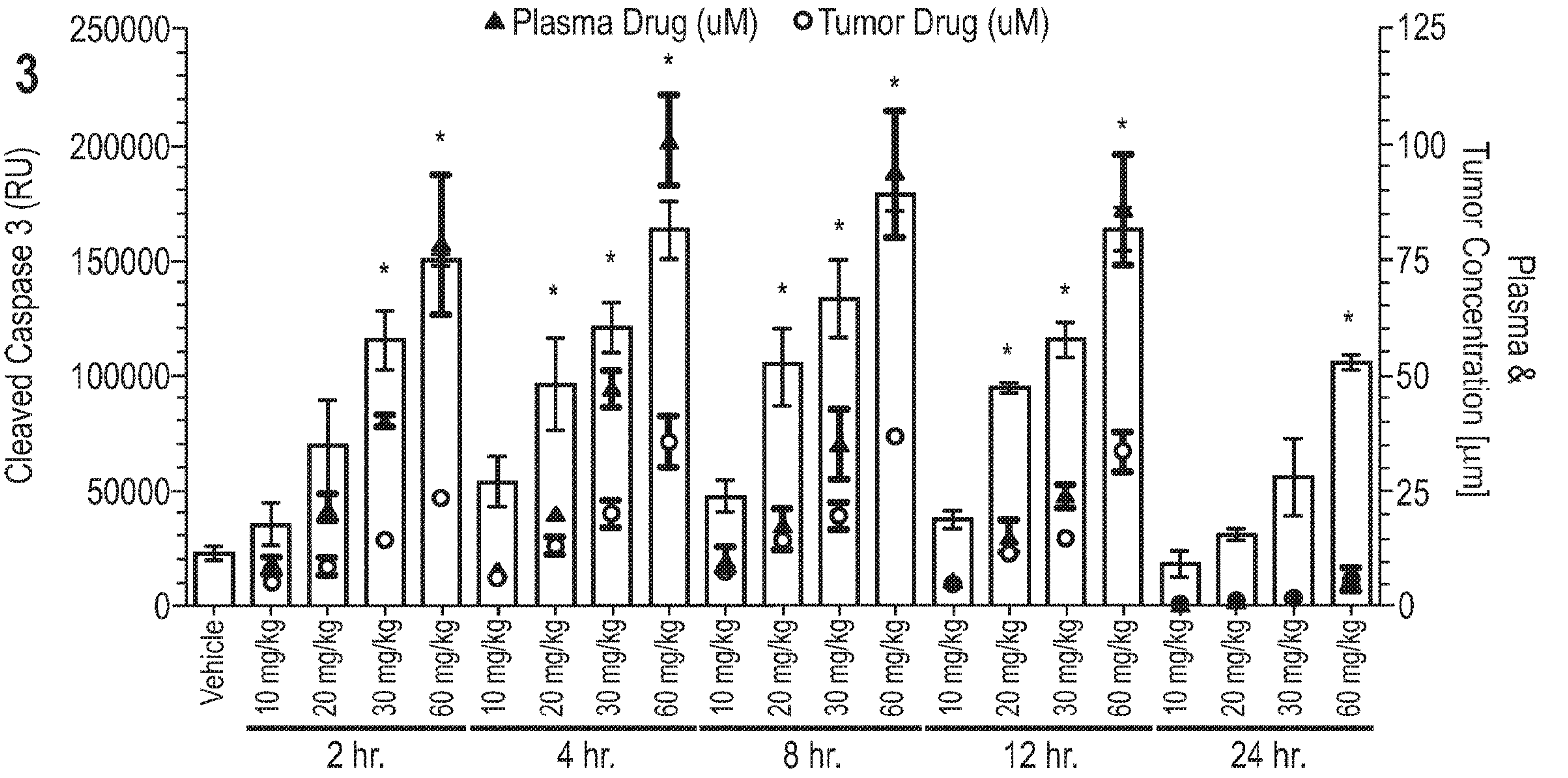

ANOVA = analysis of variance; OPM2-Luc = OPM2 cell stably transduced with the luciferase gene; PD = pharmacodynamics; RU = response unit

*p<0.05: One-way ANOVA w/ Dunnett's post-hoc n=3

OPM2-Luc tumor xenograft mice were treated with single doses of AMG 176 for the indicated times. Tumors were excised and snap frozen for cleaved caspase 3 analysis (n = 3) using a Meso Scale Discovery Immunoassay. Data represents mean± SE of the mean of caspase 3 cleavage for each group. Average plasma and tumor concentrations of AMG 176 were determined at each time and dose, and are plotted on the right y-axis.

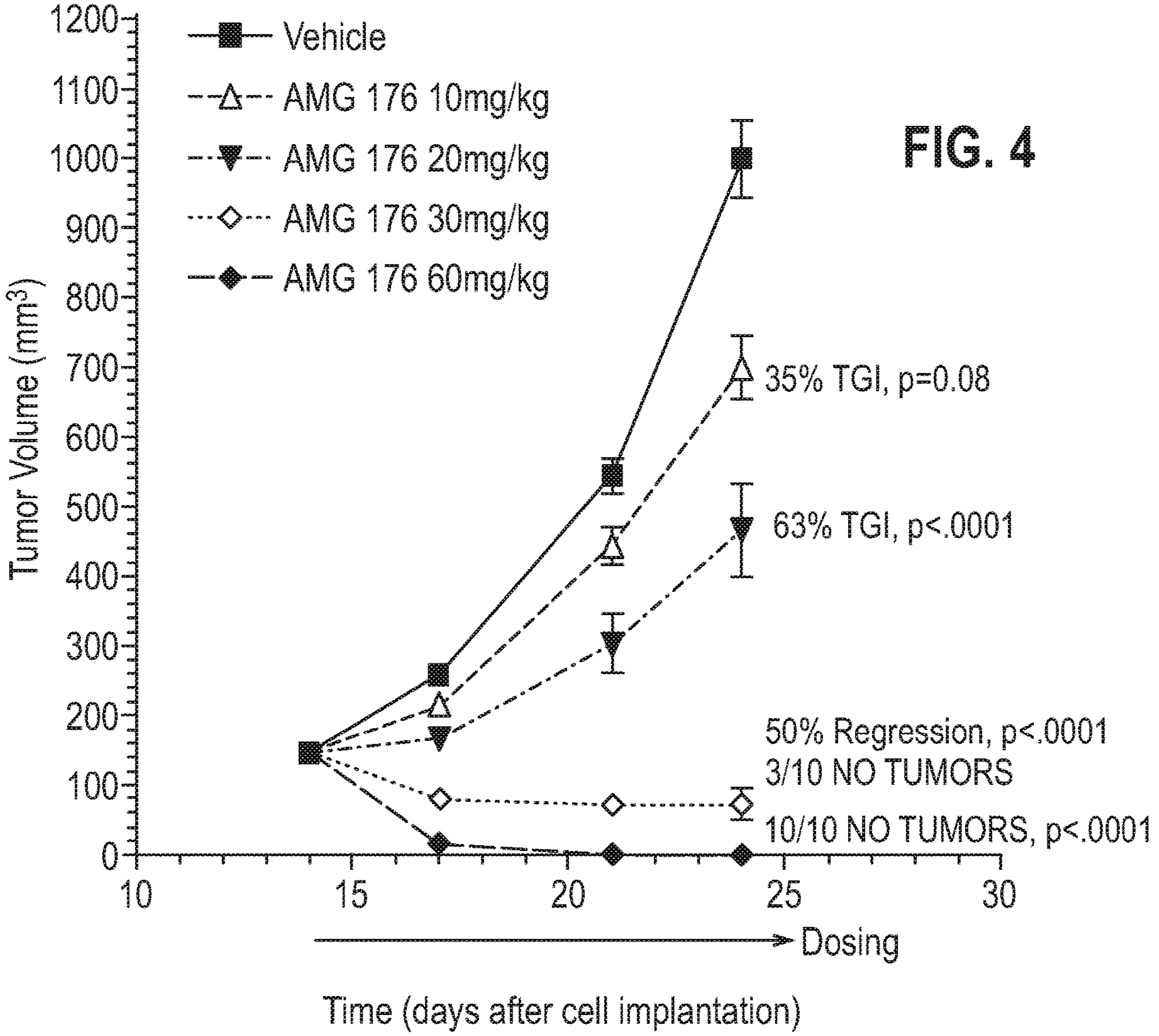

FIG. 4

MCL 1 = myeloid cell leukemia 1; OPM2-Luc = human MCL 1-dependent multiple myeloma cell line stably transduced with the luciferase gene; RMANOVA = repeated measures analysis of variance;
SC = subcutaneously; TGI = tumor growth inhibition OPM2-Luc cells ($5 \times 10^6$) were re-suspended in 50 µL of serum-free medium 1 :1 with Matrigel™ and injected SC in the right flank of female athymic nude mice. Animals were randomized based on tumor volume on day 14 (n = 10/group). Animals were treated orally, once daily with vehicle or AMG 176 at 10, 20, 30, or 60 mg/kg. Tumor volume was measured twice per week and data represent mean ± SE for each group. Percentage TGI was calculated as:
100 - ([volume - initial volume] / [control volume - initial control volume] x 100).
Percentage regression was calculated as: 100 - ([final volume / initial volume] x 100).
Statistical significance was determined by RMANOVA followed by Dunnett's post-hoc test.

FIG. 5

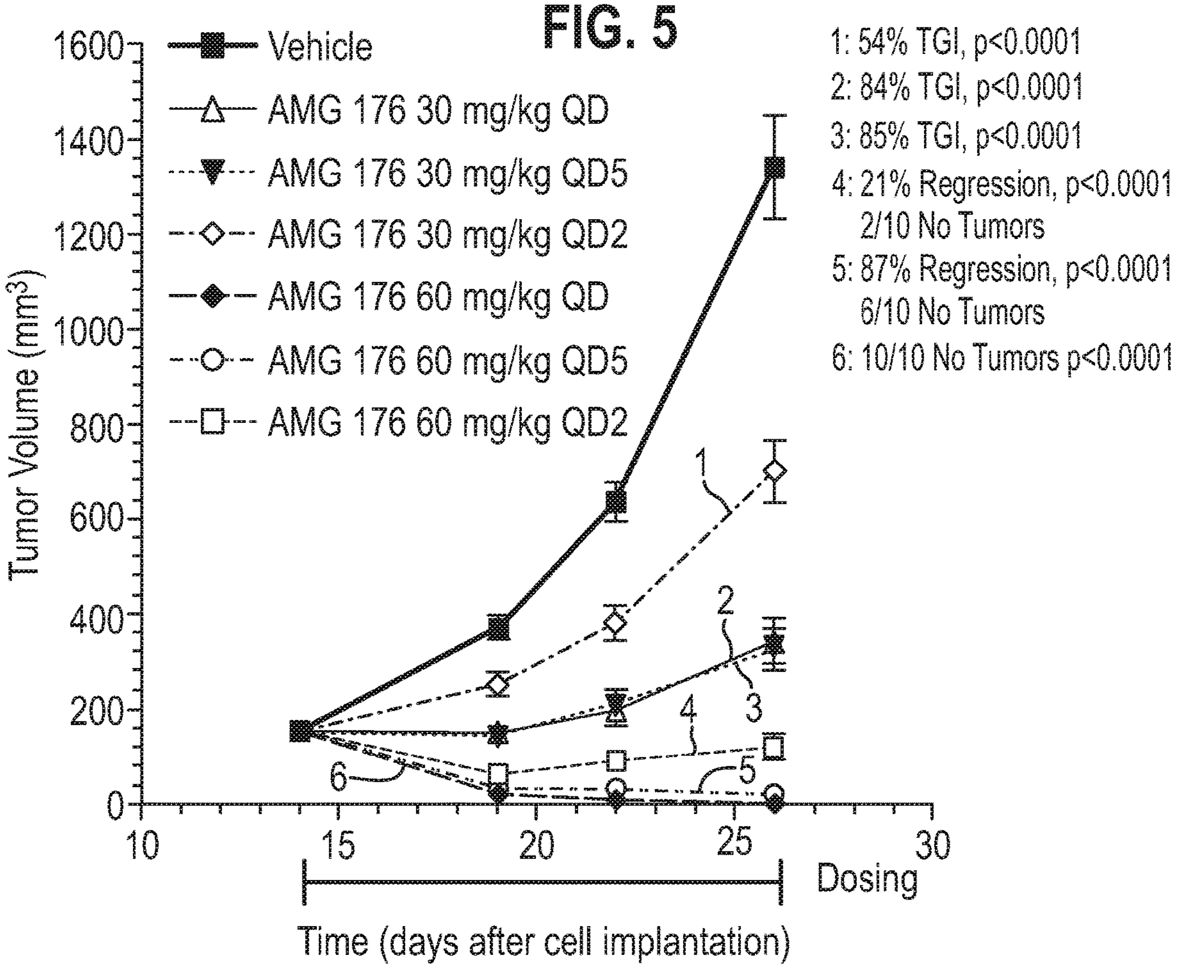

MCL1 = myeloid cell leukemia 1: OPM2-Luc = human MCL 1-dependent multiple myeloma cell line stably transduced with the luciferase gene; QD= once daily; QD5 = 5 days on, 2 days off (5x/week); QD2 = 2 days on/5 days off (2x/week); RMANOVA = repeated measures analysis of variance; SC= subcutaneously; TGI = tumor growth inhibition OPM2-Luc cells (5 x $10^6$) were re-suspended in 50μL of serum-free medium 1:1 with Matrigel™ and injected SC in the right flank of female athymic nude mice. Animals were randomized based on tumor volume on day 14 (n = 10/group). Animals were treated orally, QD with vehicle; QD, 005, or QD2 with AMG 176 30 mg/kg; and QD, QD5, or QD2 with AMG 176 at 60 mg/kg. Tumor volume was measured twice per week and data represent mean ± SE for each group. Percentage TGI was calculated as: 100 - ([volume - initial volume] / [control volume - initial control volume] x 100). Percentage regression was calculated as: 100 - ([final volume / initial volume] x 100). Statistical significance was determined by RMANIOVA followed by Dunnett's post-hoc test.

FIG. 6

Figure 5-6. Effect of AMG 176 Treatment on Tumor Size in Female Athymic Nude Mice

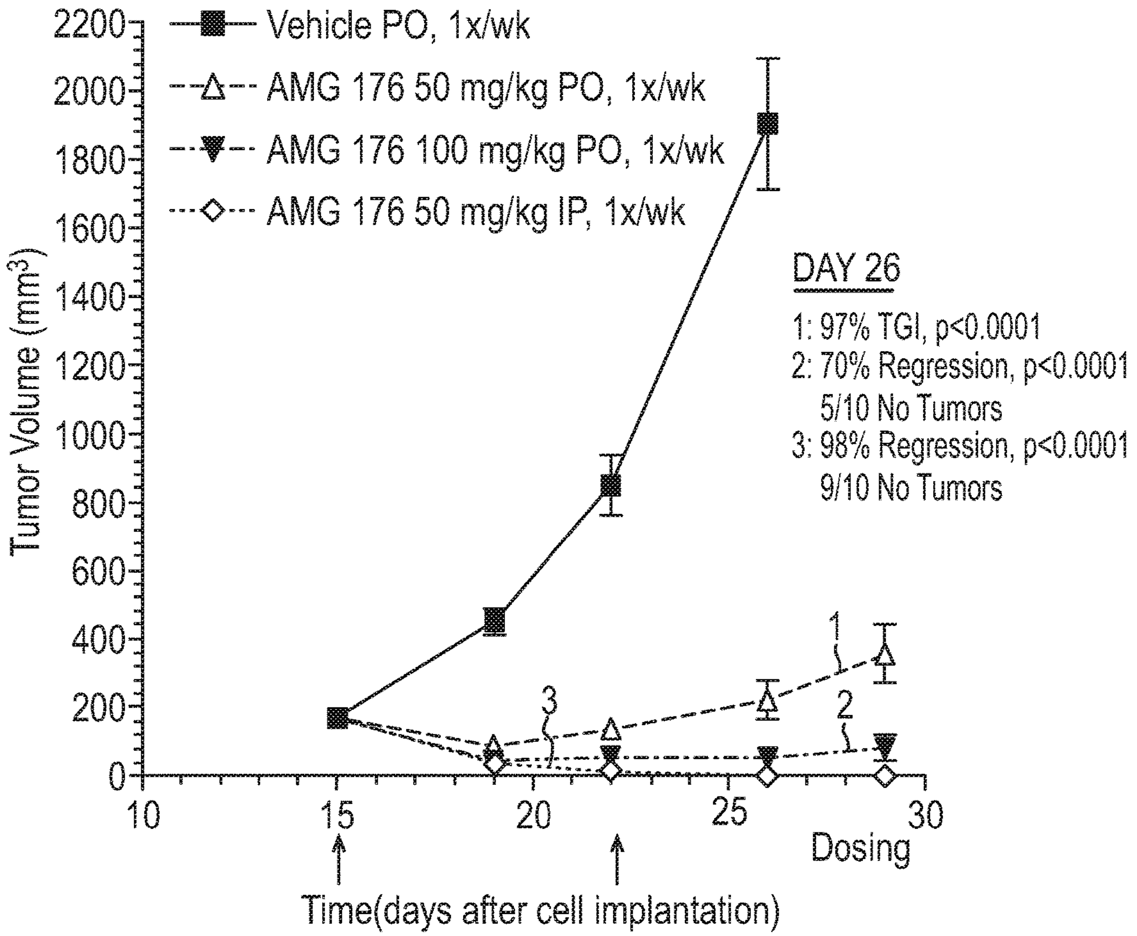

1 x/wk = once weekly; IP = intraperitoneal; MCL 1 = myeloid cell leukemia 1; OPM2-Luc = human MCL1-dependent multiple myeloma cell line stably transduced with the luciferase gene; PO = oral; TGI = tumor growth inhibition OPM2-Luc cells (5 x $10^6$) were re-suspended in 100 µL of serum-free media with 1:1 Matrigel and injected subcutaneously in the right flank of female athymic nude mice. Animals were randomized based on tumor volume on day 15 (n = 10). Animals were treated with vehicle or AMG 176 at 50, 100 mg/kg PO or 50 mg/kg IP. All compounds were administered once weekly. Tumor volume was measured twice per week and data represent mean ± SE for each group.

p values stated on day 26 are compared with vehicle group.

FIG. 7

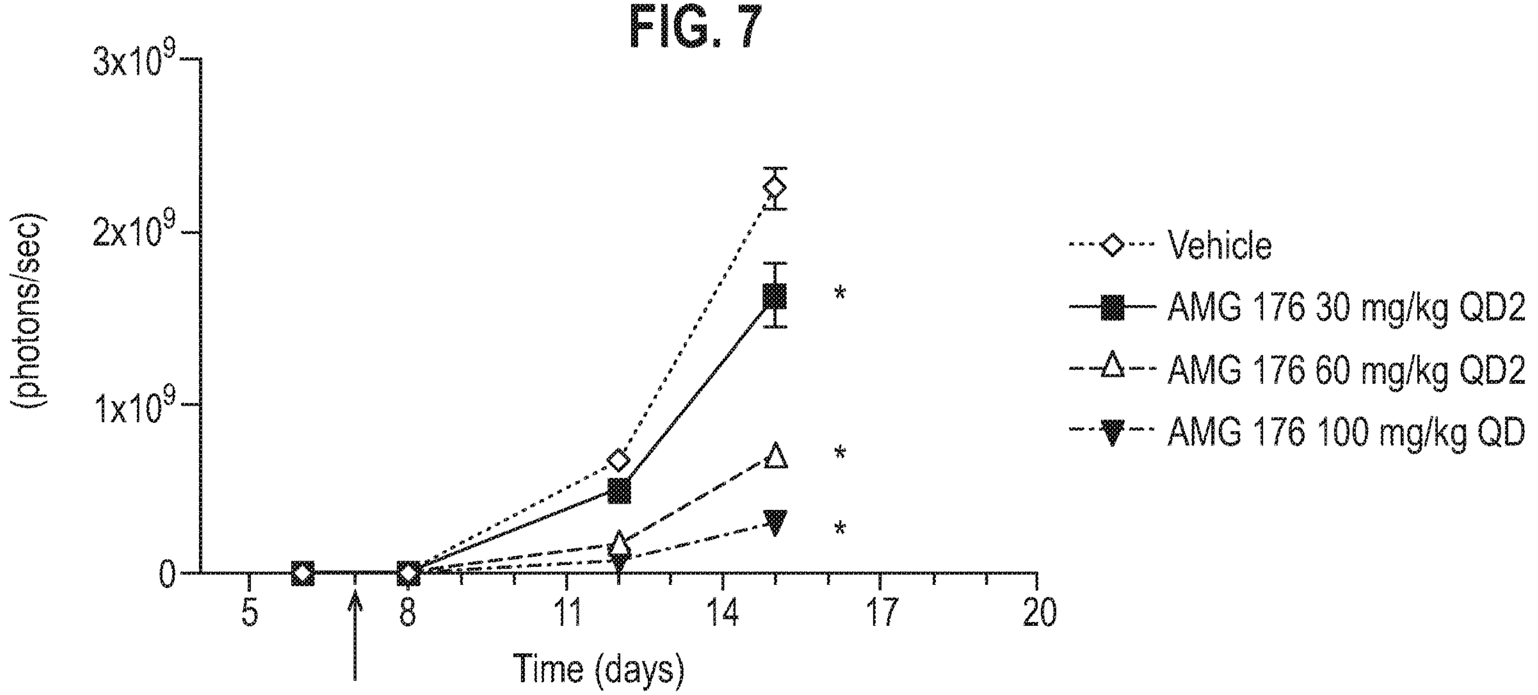

IV= intravenously; QD2 = 2 days on/5 days off (2x/week); QD = once daily; NSG = NOD/SCID IL2rg; PO = orally; sec = second Molm13-Luc cells ($5 \times 10^4$) were re-suspended in 100 µL of serum-free media and injected IV into the tail vein of NSG mice. Animals were randomized based on whole body bioluminescence on day 6 (n = 10). Animals were treated starting on day 7 (arrow) and treatment continued until day 15. Vehicle or AMG 176 at 30, 60 and 100 mg/kg were administered PO, QD, or QD2. Tumor whole body bioluminescence was measured twice per week and data represent mean ± SE for each group.

*$p < 0.0001$ compared with vehicle group

FIG. 8

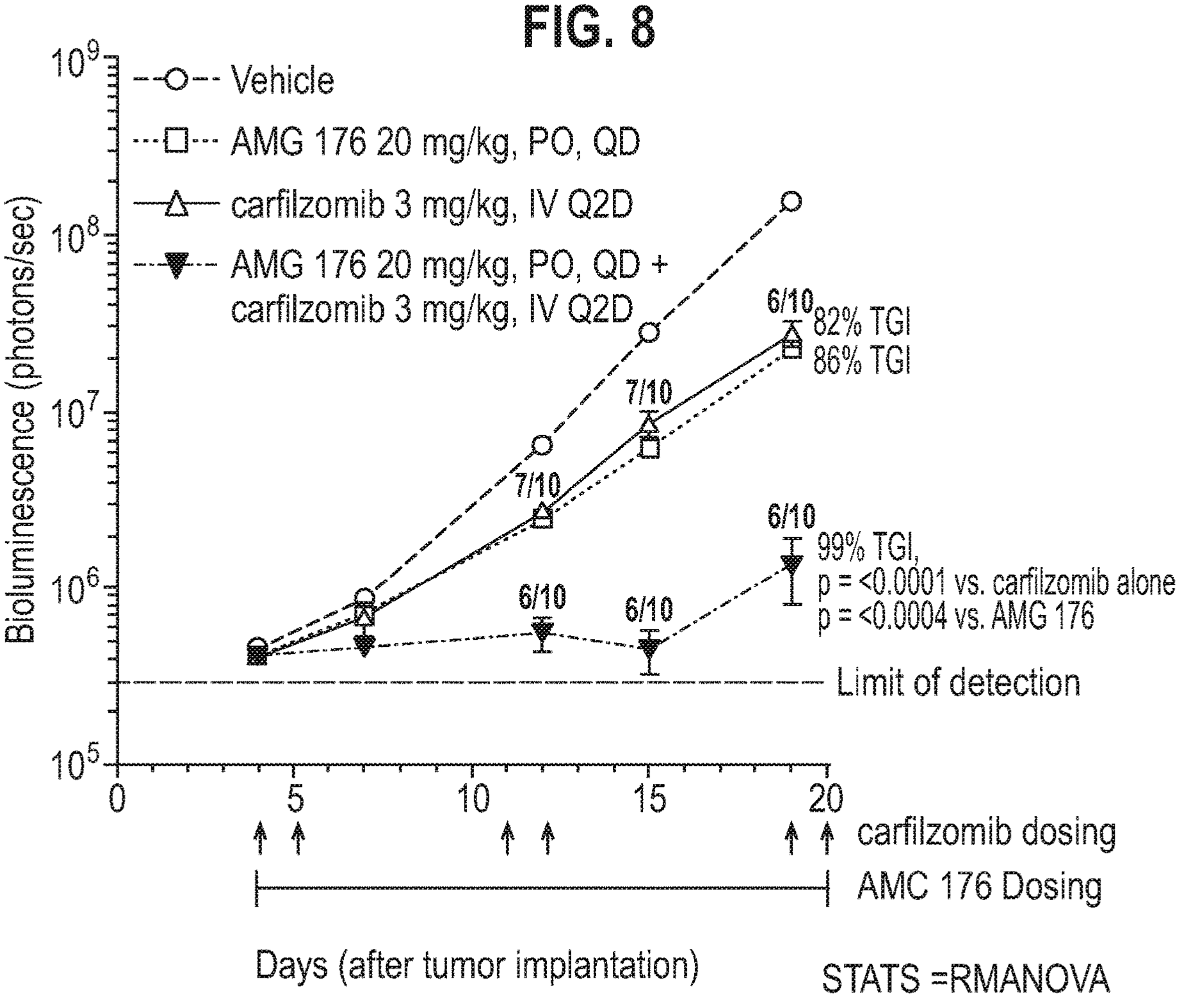

DIC= dead in cage; IV= intravenously; Q2D = 2 days on/5 days off (2x/week); QD = once daily; NSG = NOD/SCID IL2rg; PO= orally; sec = second; RMANOVA = repeated measures analysis of variance; TGI = tumor growth inhibition OPM2-Luc cells ($1 \times 10^6$) were re-suspended in 100 μL of serum-free media and injected IV into the tail vein of NSG mice. Animals were randomized based on tumor whole body bioluminescence on day 4 (n = 10). Animals were treated starting on day 4 and continued until day 20. Vehicle or AMG 176 at 20 mg/kg were administered PO, QD. Vehicle or carfilzomib at 3 mg/kg were administered IV, twice weekly. Tumor whole body bioluminescence was measured twice per week and data represents mean± SE for each group.

Observed unscheduled deaths in carfilzomib alone and combination groups:

carfilzomib alone: DIC: day 7 (n = 2), day 10 (n = 1 ), day 16 (n = 1)

carfilzomib + AMG 176 combination: DIC day 7 (n = 1 ), day 8 (n = 2), day 10 (n = 1)

Ratios above the plotted lines represent number of mice tumor free at that time point.

FORMULATIONS AND DOSAGES FOR ADMINISTERING A COMPOUND THAT INHIBITS MCL1 PROTEIN

FIELD OF THE INVENTION

The present invention relates to novel formulations including compounds of Formula I and/or salts thereof and to methods of treating cancer including hematological malignancies such as acute myelogenous leukemia, multiple myeloma, and Non-Hodgkin's lymphoma in patients with such malignancies. The invention also relates to dosage amounts and schedules for treating such diseases.

BACKGROUND OF THE INVENTION

Programmed cell death or apoptosis is regulated by a complex network of protein-protein interactions between the pro- and anti-apoptotic subgroups that form the B-cell lymphoma/leukemia 2 (BCL2) protein family (Czabotar et al, Nat'l Rev Mol Cell Biol. 15:49-63 (2014); Strasser et al, EMBO J. 30:2667-3683 (2011); Kozopas et al, Proc Nat'l Acad Sci USA 90:3516-3520 (1993)). Myeloid cell leukemia 1 (MCL1) is an anti-apoptotic member of this family and promotes cell survival. In contrast, pro-apoptotic family members such as the mitochondrial-pore forming factors BCL2 homologous antagonist/killer (BAK), BCL2-associated X (BAX), or the BCL2 homology 3 (BH3)-only protein family members, such as BCL2-interacting mediator of cell death (BIM) and p53-upregulated modulator of apoptosis (PUMA), are critical effectors for the induction of apoptosis. Upon the induction of apoptotic stimuli, pro-apoptotic BH3-only proteins bind MCL1 and other pro-survival BCL2 family members, disrupting interactions between MCL1 and the pro-apoptotic effector proteins, BAK and BAX. This disruption leads to activation and oligomerization of BAK and BAX; mitochondrial other outer membrane permeabilization (MOMP); the release of cytochrome C; caspase activation; and cell death (Czabotar et al (2014); Strasser et al, (2011)).

Myeloid cell leukemia 1 is expressed in a range of human and mouse tissues. In the mouse, for example, conditional gene-knockout studies have shown that MCL1 is important for the survival of a number of cell types including lymphocytes, hematopoietic stem cells, neutrophils, and cardiomyocytes (Thomas et al, Genes Dev 27:1365-1377 (2014); Wang et al, Genes Dev 27:1351-1364 (2013); Strasser et al, (2011)). Over-expression of MCL1 has also been implicated in the development of a number of solid and hematopoietic cancers (Ashkenazi et al. Nature Rev 15:273-284 (2017); Merino et al, Sci Transl Med 9:1-10 (2017); Kotschy et al, Nature 538:477-482 (2016); Glaser et al, Genes Dev. 26:120-125 (2012)).

The compound of Formula I and salts of the compound of Formula I are compounds that inhibit MC11 protein. The structure of the compound of Formula I is shown below:

I

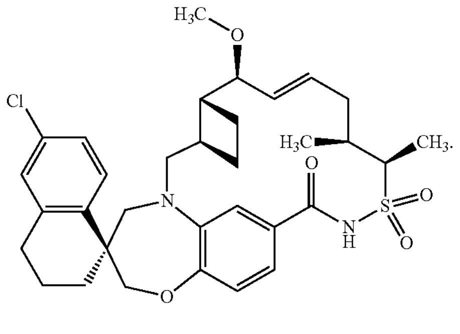

Compounds of Formula I and salts thereof and methods for synthesizing the compound are described in WO 2016/033486 and U.S. Pat. No. 9,562,061. These references are incorporated by reference herein in their entireties as if specifically set forth.

A need for suitable formulations, doses, and dosing schedules that include compounds that inhibit MCL1 protein such as the compound of Formula I and/or salts of the compound of Formula I exists. Also needed are formulations and amounts of such formulations useful for treating cancer and particularly hematological malignancies such as acute myelogenous leukemia (AML), multiple myeloma (MM), and non-Hodgkin's lymphoma (NHL) among others.

SUMMARY OF THE INVENTION

In one aspect, the invention provides a pharmaceutical formulation, the formulation comprising:

a) a compound of Formula I or a salt thereof, wherein the compound of Formula I has the following structure:

I

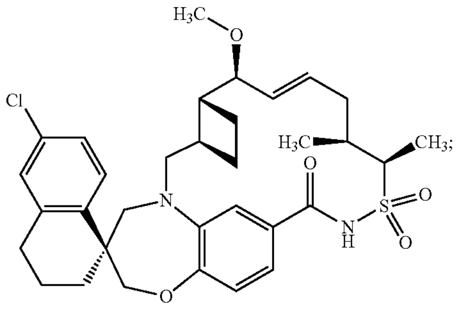

b) a cyclodextrin compound;
c) a buffer; and
d) water, wherein, the concentration of the compound of Formula I or the salt thereof in the formulation ranges from 15 mg/mL to 30 mg/mL and the pH of the formulation ranges from 8.7 to 9.9.

In another aspect, the invention provides an aqueous solution of a therapeutic agent, the solution comprising:

(a) a compound of Formula I or a salt thereof, wherein the compound of Formula I has the following structure:

I

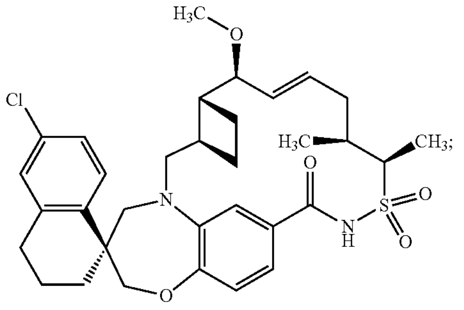

b) a cyclodextrin compound;
c) a buffer;
d) sodium chloride; and
e) water, wherein, the amount of the compound of Formula I or the salt of the compound of Formula I in the solution ranges from 25 mg to 400 mg.

In yet another aspect, the invention provides a method for making an aqueous solution suitable for intravenous infusion into a patient, the method comprising: combining the pharmaceutical formulation of any one of embodiments 1-36 with a saline solution.

In yet another aspect, the invention provides a method of treating a cancer patient, the method comprising: administering to the patient an aqueous solution comprising the compound of Formula I or a salt of the compound of Formula I, wherein the compound of Formula I has the following structure:

I

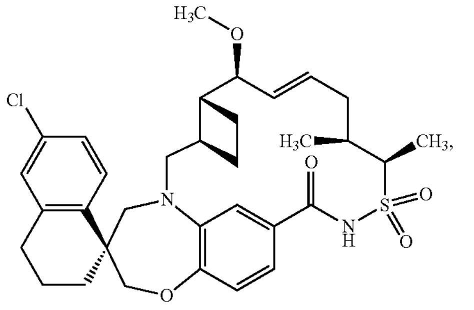

and further wherein, the compound of Formula I or the salt of the compound of Formula I is present in an amount ranging from 25 $mg/m^2$ to 960 $mg/m^2$.

In still another aspect, the invention provides an aqueous solution of a therapeutic agent, the solution comprising: a compound of Formula I or a salt thereof, wherein the compound of Formula I has the following structure:

I

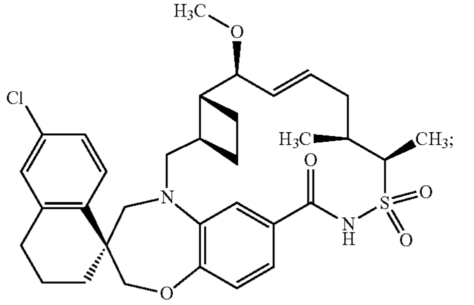

wherein, the compound of Formula I or the salt of the compound of Formula I is present in an amount ranging from 25 $mg/m^2$ to 960 $mg/m^2$.

Other objects, features and advantages of the invention will become apparent to those skilled in the art from the following description and claims.

BRIEF DESCRIPTION OF THE DRAWINGS

FIG. 2 is a graph showing BAK Activation in OPM2-Luc tumor xenografts treated with AMG 176.

FIG. 3 is a graph showing induction of cleavage Caspase 3 in OPM2-Luc Tumor Xenografts treated with AMG 176.

FIG. 4 is a graph showing tumor growth inhibition in OPM2-Luc xenografts receiving once daily dosing of AMG 176.

FIG. 5 is a graph showing tumor growth inhibition in OPM2-Luc xenografts receiving intermittent dosing of AMG 176.

FIG. 6 is a graph showing the effect of AMG 176 treatment on tumor size in Female athymic nude mice.

FIG. 7 is a graph showing the effect of AMG 176 treatment on tumor burden in NOD/SCID IL2rg (NSG) mice as measured by whole body bioluminescence imaging.

FIG. 8 is a graph showing the effect of AMG 176 plus carfilzomib combination treatment on tumor burden in NOD/SCID IL2rg (NSG) mice as measured by whole body bioluminescence imaging.

DETAILED DESCRIPTION OF THE INVENTION

Figure 1:
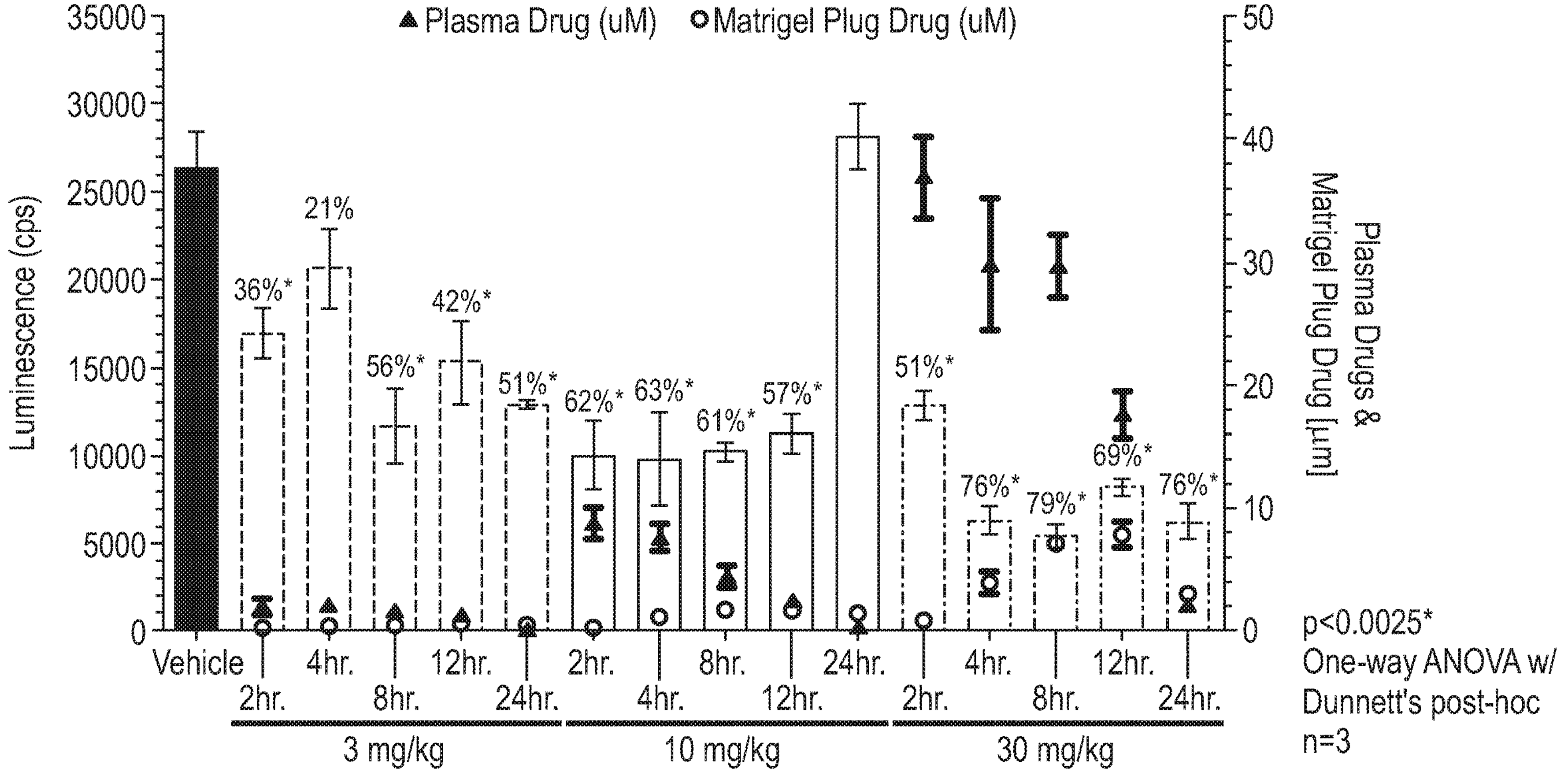
FIG. 1 is a graph showing disruption by AMG 176 of MCL1-BAK interactions in Matrigel™ plugs containing human HEK 293M MCL1(1-327)-Luc/BAK-Luc Cells Implanted in Female Athymic Nude Mice.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements. Typically, such numerical quantities will not deviate by more than 5 percent of the value provided.

The term "comprising" is meant to be open ended, i.e., all encompassing and non-limiting. It may be used herein synonymously with "having" or "including". Comprising is intended to include each and every indicated or recited component or element(s) while not excluding any other components or elements. For example, if a composition is said to comprise A and B. This means that the composition has A and B in it, but may also include C or even C, D, E, and other additional components.

Compounds for use in the present inventions include, but are not limited to, compounds of Formula I. For example, pharmaceutically acceptable salts may also be used. The term "pharmaceutically acceptable salts" refers to a salt of the compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

A buffer is a solution or a material that may be used to create a solution that contains either a weak acid and its salt or a weak base and its salt. The buffer solution is resistant to changes in pH. Typically, a buffer is an aqueous solution of either a weak acid and its conjugate base or a weak base and its conjugate acid. Buffers are typically used to maintain a stable pH in a solution as they can neutralize small quantities of additional acid or base. For a given buffer solution, there is a working pH range and a set amount of acid or base that can be neutralized before the pH will change. The amount of the acid or base that can be added to a buffer before changing its pH is called its buffer capacity. Examples of some buffers include, but are not, limited to citric acid, acetic acid $KH_2PO_4$, borate, and glycine. Glycine is a preferred buffer in the embodiments of the present invention. Any safe, nontoxic, nonreactive buffer suitable for providing a stabilized pH of around 9 may be used in accordance with the invention.

The phrase "cyclodextrin" refers to a member of a family of compounds that include cyclic oligosaccharides that include a macrocyclic ring of glucose subunits joined by α-1,4-glcosidic bonds. Cyclodextrins are typically produced from starch by enzymatic conversion. They are used in the food, pharmaceutical, drug delivery, and chemical industries, as well as in agriculture and environmental engineering. Cyclodextrins include 5 or more linked α-D-glucopyranoside units. Typically, cyclodextrins contain 6 to 8 glucose monomers. However, cyclodextrins continuing 32 or more 1,4-anhydroglucopyranoside units are known. In some embodiments, the cyclodextrin compound is hydroxypropyl-β-cyclodextrin which is commercially available from a number of suppliers including Sigma Aldrich (Saint Louis, Missouri). Generally, any cyclodextrin that solubilizes the compound of Formula I or the salt of the compound of Formula I, may be used in accordance with the invention provided it is nontoxic and suitable for administration to humans. The solubility of natural cyclodextrins tends to be poor. However, chemical substitutions at the 2, 3, and 6 hydroxyl sites greatly increases solubility.

Preferably, the cyclodextrin compound is hydroxypropyl-β-cyclodextrin.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the scope of the embodiments of the present disclosure as defined by the appended claims.

EMBODIMENTS

The embodiments listed below are presented in numbered form for convenience and for ease and clarity of reference in referring back to multiple embodiments. This disclosure constitutes a disclosure of each and every combination of technically compatible embodiments (including those below), even where those embodiments are not explicitly disclosed in combination or explicitly linked to each other.

In a first aspect and embodiment, the invention provides a pharmaceutical formulation, the formulation comprising:

a) a compound of Formula I or a salt thereof, wherein the compound of Formula I has the following structure:

I

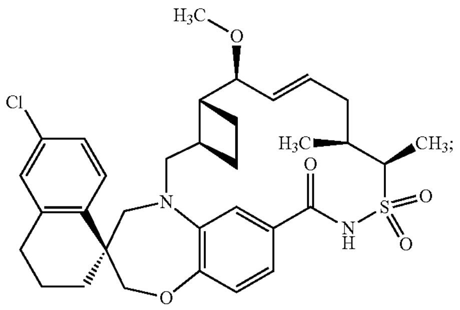

b) a cyclodextrin compound;

c) a buffer; and d) water, wherein, the concentration of the compound of Formula I or the salt thereof in the formulation ranges from 15 mg/mL to 30 mg/mL and the pH of the formulation ranges from 8.7 to 9.9.

2. The pharmaceutical formulation of embodiment 1, wherein the buffer is glycine.
3. The pharmaceutical formulation of embodiment 1 or embodiment 2, wherein the cyclodextrin compound is hydroxypropyl-β-cyclodextrin.
4. The pharmaceutical formulation of any one of embodiments 1-3, wherein the pH of the formulation is from 8.8 to 9.8.
5. The pharmaceutical formulation of embodiment 4, wherein the pH ranges from 8.9 to 9.5.
6. The pharmaceutical formulation of embodiment 4, wherein the pH of the formulation ranges from 8.9 to 9.2.
7. The pharmaceutical formulation of embodiment 4, wherein the pH of the formulation is 9.
8. The pharmaceutical formulation of any one of embodiments 1-7, wherein the concentration of the compound of Formula I, or the salt thereof, in the formulation ranges from 20 to 30 mg/mL.
9. The pharmaceutical formulation of embodiment 8, wherein the concentration of the compound of Formula I, or the salt thereof, in the formulation ranges from 22 to 28 mg/mL.
10. The pharmaceutical formulation of embodiment 8, wherein the concentration of the compound of Formula I, or the salt thereof, in the formulation ranges from 24 to 26 mg/mL.
11. The pharmaceutical formulation of embodiment 8, wherein the concentration of the compound of Formula I, or the salt thereof, in the formulation is 25 mg/mL.
12. The pharmaceutical formulation of any one of embodiments 1-11, wherein the amount of the cyclodextrin compound in the formulation ranges from 7.5 to 13 percent weight by weight.
13. The pharmaceutical formulation of embodiment 12, wherein the amount of the cyclodextrin compound in the formulation ranges from 8 to 12 percent weight by weight.
14. The pharmaceutical formulation of embodiment 12, wherein the amount of the cyclodextrin compound in the formulation ranges from 9 to 11 percent weight by weight.
15. The pharmaceutical formulation of embodiment 12, wherein the amount of the cyclodextrin compound in the formulation is 10 percent weight by weight.

16. The pharmaceutical formulation of any one of embodiments 1-15, wherein the formulation is buffered with glycine, wherein the buffer used to buffer the formulation includes glycine at a concentration ranging from 80 mM to 120 mM.
17. The pharmaceutical formulation of embodiment 16, wherein the formulation is buffered with glycine, wherein the buffer used to buffer the formulation includes glycine at a concentration ranging from 90 mM to 110 mM.
18. The pharmaceutical formulation of embodiment 16, wherein the formulation is buffered with glycine, wherein the buffer used to buffer the formulation includes glycine at a concentration ranging from 95 mM to 105 mM.
19. The pharmaceutical formulation of embodiment 16, wherein the formulation is buffered with glycine, wherein the buffer used to buffer the formulation includes glycine at a concentration of 100 mM.
20. The pharmaceutical formulation of any one of embodiments 1-19, wherein the volume of the formulation ranges from 5 mL to 25 mL.
21. The pharmaceutical formulation of embodiment 20, wherein the volume of the formulation ranges from 8 mL to 20 mL.
22. The pharmaceutical formulation of embodiment 20, wherein the volume of the formulation ranges from 9 mL to 15 mL.
23. The pharmaceutical formulation of embodiment 20, wherein the volume of the formulation is 10 mL
24. The pharmaceutical formulation of embodiment 20, wherein the volume of the formulation ranges 14 mL to 15 mL.
25. The pharmaceutical formulation of embodiment 20, wherein the volume of the formulation is 14.4 mL.
26. The pharmaceutical formulation of embodiment 1, wherein the formulation is an aqueous formulation comprising from 20 mg/mL to 30 mg/mL of the compound of Formula I and from 8 percent to 12 percent weight by weight hydroxypropyl-β-cyclodextrin and is buffered with 90 mM to 110 mM glycine to a pH of 8.8 to 9.2.
27. The pharmaceutical formulation of embodiment 1, wherein the formulation is an aqueous formulation comprising 25 mg/mL of the compound of Formula I and 10 percent weight by weight hydroxypropyl-β-cyclodextrin buffered with 100 mM glycine to a pH of 9.
28. The pharmaceutical formulation of embodiment 26 or embodiment 27, wherein the amount of the formulation ranges from 9 mL to 15 mL.
29. The pharmaceutical formulation of embodiment 26 or embodiment 27, wherein the amount of the formulation is 10 mL.
30. The pharmaceutical formulation of embodiment 26 or embodiment 27, wherein the amount of the formulation is 14.4 mL.
31. The pharmaceutical formulation of any one of embodiments 1-30, wherein the formulation is contained within a vial.
32. The pharmaceutical formulation of embodiment 31, wherein the vial is a 20 mL borosilicate glass vial or a 20 mL aluminosilicate glass vial, wherein the vial is equipped with a stopper and an aluminum seal with a flip off cover.
33. In a second aspect and thirty third embodiment, the invention provides an aqueous solution of a therapeutic agent, the solution comprising:
(a) a compound of Formula I or a salt thereof, wherein the compound of Formula I has the following structure:

I

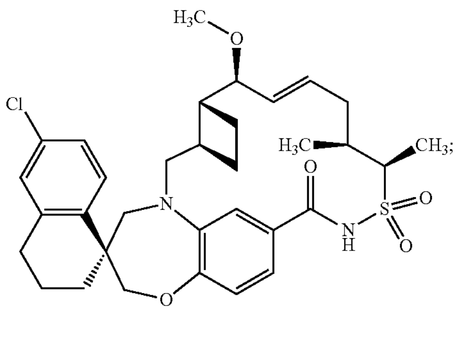

b) a cyclodextrin compound;
c) a buffer;
d) sodium chloride; and
e) water, wherein, the amount of the compound of Formula I or the salt of the compound of Formula I in the solution ranges from 25 mg to 400 mg.

34. The aqueous solution of embodiment 33, wherein the buffer is glycine.
35. The aqueous solution of embodiment 33 or embodiment 34, wherein the cyclodextrin compound is hydroxypropyl-β-cyclodextrin.
36. The aqueous solution of any one of embodiments 33-35, wherein the amount of the compound of Formula I or the salt of the compound of Formula I in the solution ranges from 200 mg to 360 mg.
37. The aqueous solution of any one of embodiments 33-36, wherein the solution is contained in an IV bag.
38. In a third aspect and thirty eighth embodiment, the invention provides a method for making an aqueous solution suitable for intravenous infusion into a patient, the method comprising: combining the pharmaceutical formulation of any one of embodiments 1-32 with a saline solution. In some such embodiments, the method for making an aqueous solution suitable for intravenous infusion into a patient comprises transferring the pharmaceutical formulation of any one of embodiments 1-32 to the saline solution. In some such embodiments, the saline solution is in an IV bag.
39. The method of embodiment 38, wherein the saline solution prior to combining the pharmaceutical formulation with the saline solution comprises sodium chloride in an amount ranging from 8 g/L to 10 g/L.
40. The method of embodiment 38, wherein the saline solution prior to combining the pharmaceutical formulation with the saline solution comprises sodium chloride in an amount of 9 g/L.
41. In a fourth aspect and forty first embodiment, the invention provides a method of treating a cancer patient, the method comprising: administering to the patient an aqueous solution comprising the compound of Formula I or a salt of the compound of Formula I, wherein the compound of Formula I has the following structure:

I

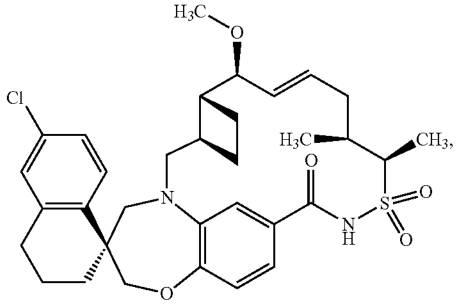

and further wherein, the compound of Formula I or the salt of the compound of Formula I is present in an amount ranging from 25 $mg/m^2$ to 960 $mg/m^2$.

42. The method of embodiment 41, wherein the cancer is a hematological malignancy.
43. The method of embodiment 42, wherein the hematological malignancy is acute myelogenous leukemia, multiple myeloma, or non-Hodgkin's lymphoma.
44. The method of embodiment 42, wherein the hematological malignancy is acute myelogenous leukemia.
45. The method of embodiment 44, wherein the patient has relapsed or refractory acute myelogenous leukemia.
46. The method of embodiment 42, wherein the hematological malignancy is multiple myeloma.
47. The method of embodiment 46, wherein the patient has relapsed or refractory multiple myeloma.
48. The method of embodiment 42, wherein the hematological malignancy is acute myelogenous leukemia, multiple myeloma, or non-Hodgkin's lymphoma.
49. The method of embodiment 41, wherein the cancer is selected from breast cancer, colorectal cancer, skin cancer, melanoma, ovarian cancer, kidney cancer, lung cancer, non-small cell lung cancer, non-Hodgkin's lymphoma, multiple myeloma, or acute myelogenous leukemia
50. The method of embodiment 41, wherein the compound of Formula I or the salt of the compound of Formula I is present in an amount ranging from 50 $mg/m^2$ to 250 $mg/m^2$.
51. The method of embodiment 50, wherein the compound of Formula I or the salt of the compound of Formula I is present in an amount ranging from 50 $mg/m^2$ to 200 $mg/m^2$.
52. The method of embodiment 50, wherein the compound of Formula I or the salt of the compound of Formula I is present in an amount ranging from 60 $mg/m^2$ to 180 $mg/m^2$.
53. The method of embodiment 50, wherein the compound of Formula I or the salt of the compound of Formula I is present in an amount of 60 $mg/m^2$.
54. The method of embodiment 50, wherein the compound of Formula I or the salt of the compound of Formula I is present in an amount of 120 $mg/m^2$.
55. The method of embodiment 50, wherein the compound of Formula I or the salt of the compound of Formula I is present in an amount of 180 $mg/m^2$.
56. The method of any one of embodiments 41-55, wherein the method further comprises administering the aqueous solution comprising the compound of Formula I or the salt of the compound of Formula I to the patient at least twice a week.
57. The method of any one of embodiments 41-55, wherein the aqueous solution comprising the compound of Formula I or the salt of the compound of Formula I further comprises:

a) a cyclodextrin compound;

b) a buffer; and c) sodium chloride.

58. The method of embodiment 57, wherein the cyclodextrin compound is hydroxypropyl-β-cyclodextrin.
59. The method of embodiment 57 or embodiment 58, wherein the buffer is glycine.
60. The method of any one of embodiments 41-56, wherein the method comprises administering the aqueous solution comprising the compound of Formula I or the salt of the compound of Formula I to the patient once or twice a week for at least 1 to 6 weeks.
61. The method of embodiment 60, wherein the aqueous solution comprising the compound of Formula I or the salt of the compound of Formula I to the patient is administered for at least 6 weeks.
62. The method of embodiment 60, wherein the aqueous solution comprising the compound of Formula I or the salt of the compound of Formula I to the patient is administered for at least 5 weeks.
63. The method of embodiment 60, wherein the aqueous solution comprising the compound of Formula I or the salt of the compound of Formula I to the patient is administered for at least 4 weeks.
64. The method of embodiment 60, wherein the aqueous solution comprising the compound of Formula I or the salt of the compound of Formula I to the patient is administered for at least 3 weeks.
65. The method of embodiment 60, wherein the aqueous solution comprising the compound of Formula I or the salt of the compound of Formula I to the patient is administered for at least 2 weeks.
66. The method of any one of embodiments 41-65, further comprising administering the aqueous solution comprising the compound of Formula I or the salt of the compound of Formula I to the patient once or twice a day.
67. The method of any one of embodiments 41-66, wherein the aqueous solution comprising the compound of Formula I or the salt of the compound of Formula I is administered on at least two consecutive days.
68. The method of any one of embodiments 41-67, wherein the aqueous solution comprising the compound of Formula I or the salt of the compound of Formula I is administered intravenously.
69. The method of embodiment 68, wherein the aqueous solution comprising the compound of Formula I or the salt of the compound of Formula I is administered intravenously for a period of at least two hours.
70. In a fifth aspect and a seventieth embodiment, the invention provides an aqueous solution of a therapeutic agent, the solution comprising: a compound of Formula I or a salt thereof, wherein the compound of Formula I has the following structure:

I

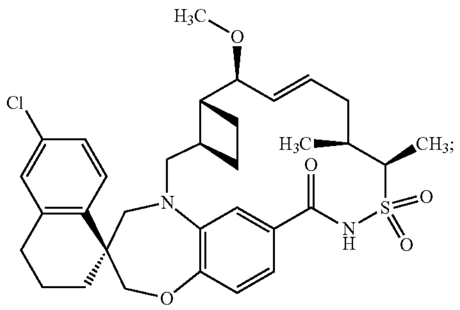

wherein, the compound of Formula I or the salt of the compound of Formula I is present in an amount ranging from 25 $mg/m^2$ to 960 $mg/m^2$.

71. The aqueous solution of embodiment 70, wherein the compound of Formula I or the salt of the compound of Formula I is present in an amount ranging from 25 $mg/m^2$ to 250 $mg/m^2$.
72. The aqueous solution of embodiment 70, wherein the compound of Formula I or the salt of the compound of Formula I is present in an amount ranging from 50 $mg/m^2$ to 200 $mg/m^2$.
73. The aqueous solution of embodiment 70, wherein the compound of Formula I or the salt of the compound of Formula I is present in a dose ranging from 60 $mg/m^2$ to 180 $mg/m^2$.
74. The aqueous solution of embodiment 70, wherein the compound of Formula I or the salt of the compound of Formula I is present in a dose of 60 $mg/m^2$.
75. The aqueous solution of embodiment 70, wherein the compound of Formula I or the salt of the compound of Formula I is present in a dose of 120 $mg/m^2$.
76. The aqueous solution of embodiment 70, wherein the compound of Formula I or the salt of the compound of Formula I is present in a dose of 180 $mg/m^2$.
77. The aqueous solution of any one of embodiments 70-76, wherein the aqueous solution comprising the compound of Formula I or the salt of the compound of Formula I further comprises:

a) a cyclodextrin compound;

b) a buffer; and c) sodium chloride.

78. The aqueous solution of embodiment 77, wherein the buffer is glycine.
79. The aqueous solution of embodiment 77 or embodiment 78, wherein the cyclodextrin compound is hydroxypropyl-β-cyclodextrin.
80. An aqueous solution for use in a method of treating cancer in a patient, wherein the aqueous solution comprises the compound of Formula I or a salt of the compound of Formula I, wherein the compound of Formula I has the following structure:

I

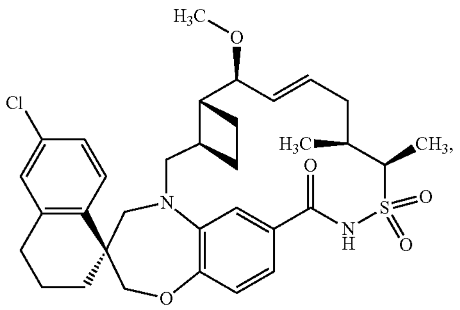

wherein the method comprises administering the compound of Formula I or the salt of the compound of Formula I in an amount ranging from 25 $mg/m^2$ to 960 $mg/m^2$.

81. The aqueous solution for use according to embodiment 80, wherein the cancer is a hematological malignancy.
82. The aqueous solution for use according to embodiment 81, wherein the hematological malignancy is acute myelogenous leukemia, multiple myeloma, or non-Hodgkin's lymphoma.
83. The aqueous solution for use according to embodiment 81, wherein the hematological malignancy is acute myelogenous leukemia.
84. The aqueous solution for use according to embodiment 83, wherein the patient has relapsed or refractory acute myelogenous leukemia.
85. The aqueous solution for use according to embodiment 81, wherein the hematological malignancy is multiple myeloma.
86. The aqueous solution for use according to embodiment 85, wherein the patient has relapsed or refractory multiple myeloma.
87. The aqueous solution for use according to embodiment 81, wherein the hematological malignancy is acute myelogenous leukemia, multiple myeloma, or non-Hodgkin's lymphoma.
88. The aqueous solution for use according to embodiment 80, wherein the cancer is selected from breast cancer, colorectal cancer, skin cancer, melanoma, ovarian cancer, kidney cancer, lung cancer, non-small cell lung cancer, non-Hodgkin's lymphoma, multiple myeloma, or acute myelogenous leukemia.
89. The aqueous solution for use according to any one of embodiments 80-88, wherein the method comprises administering the compound of Formula I or the salt of the compound of Formula I in an amount ranging from 50 $mg/m^2$ to 250 $mg/m^2$.
90. The aqueous solution for use according to embodiment 89, wherein the method comprises administering the compound of Formula I or the salt of the compound of Formula I in an amount ranging from 50 $mg/m^2$ to 200 $mg/m^2$.
91. The aqueous solution for use according to embodiment 89, wherein the method comprises administering the compound of Formula I or the salt of the compound of Formula I in an amount ranging from 60 $mg/m^2$ to 180 $mg/m^2$.
92. The aqueous solution for use according to embodiment 89, wherein the method comprises administering the compound of Formula I or the salt of the compound of Formula I in an amount of 60 $mg/m^2$.

93. The aqueous solution for use according to embodiment 89, wherein the method comprises administering the compound of Formula I or the salt of the compound of Formula I in an amount of 120 $mg/m^2$.

94. The aqueous solution for use according to embodiment 89, wherein the method comprises administering the compound of Formula I or the salt of the compound of Formula I in an amount of 180 $mg/m^2$.

95. The aqueous solution for use according to any one of embodiments 80-94, wherein the method comprises administering the aqueous solution comprising the compound of Formula I or the salt of the compound of Formula I to the patient at least twice a week.

96. The aqueous solution for use according to embodiments 80-95, wherein the aqueous solution comprising the compound of Formula I or the salt of the compound of Formula I further comprises:

a) a cyclodextrin compound;

b) a buffer; and c) sodium chloride.

97. The aqueous solution for use according to embodiment 96 wherein the cyclodextrin compound is hydroxypropyl-β-cyclodextrin.

98. The aqueous solution for use according to embodiment 96 or embodiment 97, wherein the buffer is glycine.

99. The aqueous solution for use according to any one of embodiments 80-95, wherein the method comprises administering the aqueous solution comprising the compound of Formula I or the salt of the compound of Formula I to the patient once or twice a week for at least 1 week.

100. The aqueous solution for use according to embodiment 99, wherein the aqueous solution comprising the compound of Formula I or the salt of the compound of Formula I to the patient is administered for at least 6 weeks.

101. The aqueous solution for use according to embodiment 99, wherein the aqueous solution comprising the compound of Formula I or the salt of the compound of Formula I to the patient is administered for at least 5 weeks.

102. The aqueous solution for use according to embodiment 99, wherein the aqueous solution comprising the compound of Formula I or the salt of the compound of Formula I to the patient is administered for at least 4 weeks.

103. The aqueous solution for use according to embodiment 99, wherein the aqueous solution comprising the compound of Formula I or the salt of the compound of Formula I to the patient is administered for at least 3 weeks.

104. The aqueous solution for use according to embodiment 99, wherein the aqueous solution comprising the compound of Formula I or the salt of the compound of Formula I to the patient is administered for at least 2 weeks.

105. The aqueous solution for use according to any one of embodiments 80-104, further comprising administering the aqueous solution comprising the compound of Formula I or the salt of the compound of Formula I to the patient once or twice a day.

106. The aqueous solution for use according to any one of embodiments 80-105, wherein the aqueous solution comprising the compound of Formula I or the salt of the compound of Formula I is administered on at least two consecutive days.

107. The aqueous solution for use according to any one of embodiments 80-106, wherein the aqueous solution comprising the compound of Formula I or the salt of the compound of Formula I is administered intravenously.

108. The aqueous solution for use according to embodiment 107, wherein the aqueous solution comprising the compound of Formula I or the salt of the compound of Formula I is administered intravenously for a period of at least two hours.

In some embodiments, the compound of Formula I or the salt thereof may be administered along with at least a second therapeutic agent. In some such embodiments, the second therapeutic agent is administered prior to administration of the compound of Formula I or the salt thereof. In some such embodiments, the second therapeutic agent is administered after the compound of Formula I or the salt thereof has been administered to the patient. In still other such embodiments, the second therapeutic agent is administered at the same time that the compound of Formula I or the salt thereof is administered to the patient. Various second therapeutic agents that may be used include, but are not limited to, venetoclax, carfilzomib, azacitidine, and dexamethasone.

The aqueous formulations provided herein including the compound of Formula I and/or salts of the compound may be used to treat multiple myeloma. Typically, doses for treating multiple myeloma once daily for two consecutive days and then no treatment for 5 days (QD2) include doses ranging from 30 to 960 $mg/m^2$, including, for example QD2 doses of 30, 40, 50, 60, 120, 180, 240, 360, 480, 600, 720, 840, and 960 $mg/m^2$ (IV; QD2). Typically, doses for treating multiple myeloma once weekly (QW) include doses ranging from 180 to 960 $mg/m^2$, including, for example QW doses of 180, 240, 360, 480, 600, 720, 840, and 960 $mg/m^2$. The formulations are typically administered intravenously.

The aqueous formulations provided herein including the compound of Formula I and/or salts of the compound may be also used to treat acute myelogenous leukemia. Typically, doses for treating acute myelogenous leukemia once daily for two consecutive days and then no treatment for 5 days (QD2) include doses ranging from 30 to 960 $mg/m^2$, including, for example QD2 doses of 60, 120, 180, 240, 360, 480, 600, 720, 840, and 960 $mg/m^2$ (IV; QD2). Typically, doses for treating acute myelogenous leukemia once weekly (QW) include doses ranging from 180 to 960 $mg/m^2$, including, for example QW doses of 180, 240, 360, 480, 600, 720, 840, and 960 $mg/m^2$. The formulations are typically administered intravenously.

The invention provides the compound of Formula I or a salt thereof, wherein the compound of Formula I has the following structure:

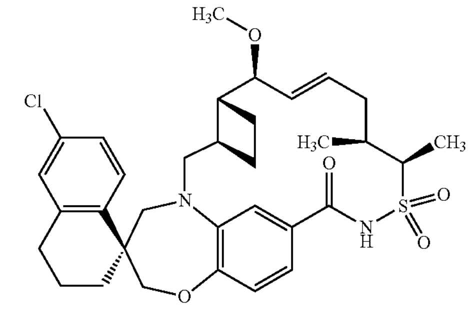 [SMILES: CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

for use in a method of therapy. Preferably, the method comprises administering the solution intravenously. The method may optionally further comprise administering a second therapeutic agent selected from the list consisting of venetoclax, carfilzomib, azacitidine, and dexamethasone. Optionally, the method may comprise administering the pharmaceutical formulation of any of embodiments 1-30 or the aqueous solution of any of embodiments 33-36.

The invention provides the compound of Formula I or a salt thereof, wherein the compound of Formula I has the following structure:

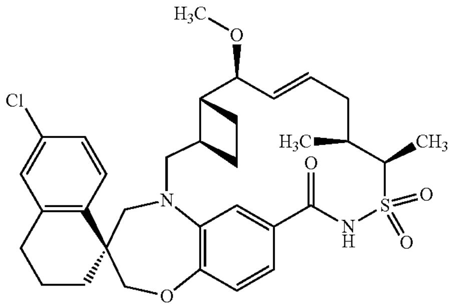 [SMILES: CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

for use in a method of treating multiple myeloma. Preferably, the method comprises administering the solution intravenously. The method may optionally further comprise administering a second therapeutic agent selected from the list consisting of venetoclax, carfilzomib, azacitidine, and dexamethasone. Optionally, the method may comprise administering the pharmaceutical formulation of any of embodiments 1-30 or the aqueous solution of any of embodiments 33-36.

The invention provides the compound of Formula I or a salt thereof, wherein the compound of Formula I has the following structure:

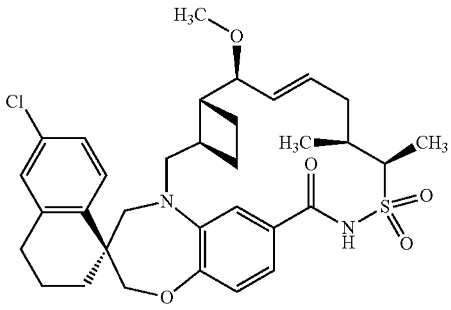 [SMILES: CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

for use in a method of treating acute myelogenous leukemia. Preferably, the method comprises administering the solution intravenously. The method may optionally further comprise administering a second therapeutic agent selected from the list consisting of venetoclax, carfilzomib, azacitidine, and dexamethasone. Optionally, the method may comprise administering the pharmaceutical formulation of any of embodiments 1-30 or the aqueous solution of any of embodiments 33-36.

The invention provides the compound of Formula I or a salt thereof, wherein the compound of Formula I has the following structure:

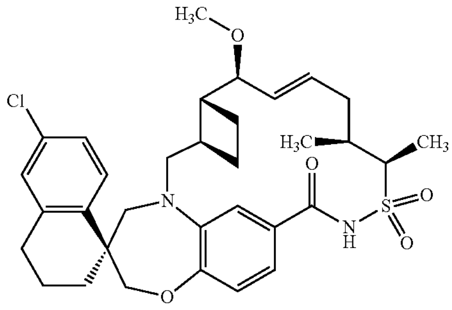 [SMILES: CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

for use in a method of treating non-Hodgkin's lymphoma. Preferably, the method comprises administering the solution intravenously. The method may optionally further comprise administering a second therapeutic agent selected from the list consisting of venetoclax, carfilzomib, azacitidine, and dexamethasone. Optionally, the method may comprise administering the pharmaceutical formulation of any of embodiments 1-30 or the aqueous solution of any of embodiments 33-36.

The invention provides an aqueous solution of a therapeutic agent, the solution comprising:

(a) a compound of Formula I or a salt thereof, wherein the compound of Formula I has the following structure:

I

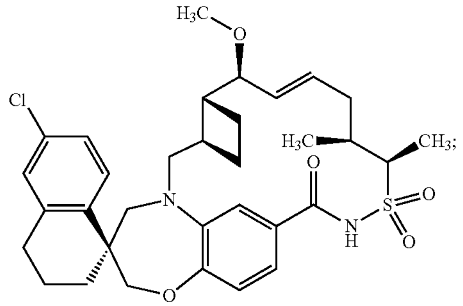

b) a cyclodextrin compound;
c) a buffer;
d) sodium chloride; and
e) water, wherein, the amount of the compound of Formula I or the salt of the compound of Formula I in the solution ranges from 25 mg to 400 mg; wherein the concentration of the compound of Formula I or the salt thereof in the solution ranges from 15 mg/mL to 30 mg/mL and the pH of the formulation ranges from 8.7 to 9.9. The invention further provides said aqueous solution for use in a method of treating cancer in a patient, preferably wherein the cancer is a hematological malignancy, most preferably wherein the cancer is selected from the list consisting of acute myelogenous leukemia, multiple myeloma and non-Hodgkin's lymphoma. Preferably, the method comprises administering said aqueous solution intravenously, and preferably the method comprises diluting the solution, e.g. in a bag containing saline, prior to intravenous administration. The method may optionally further comprise administering a second therapeutic agent selected from the list consisting of venetoclax, carfilzomib, azacitidine, and dexamethasone.

The invention provides an aqueous solution of a therapeutic agent for use in a method of therapy, the solution comprising:

(a) a compound of Formula I or a salt thereof, wherein the compound of Formula I has the following structure:

I

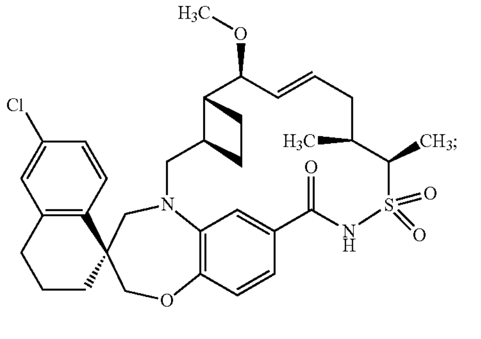

b) a cyclodextrin compound;
c) a buffer;
d) sodium chloride; and
e) water, wherein, the amount of the compound of Formula I or the salt of the compound of Formula I in the solution ranges from 25 mg to 400 mg. Preferably, the method comprises administering the solution intravenously, and preferably the method comprises diluting the solution, e.g. in a bag containing saline, prior to intravenous administration. The method may optionally further comprise administering a second therapeutic agent selected from the list consisting of venetoclax, carfilzomib, azacitidine, and dexamethasone.

The invention provides a pharmaceutical formulation for use in a method of therapy, the formulation comprising:

a) a compound of Formula I or a salt thereof, wherein the compound of Formula I has the following structure:

I

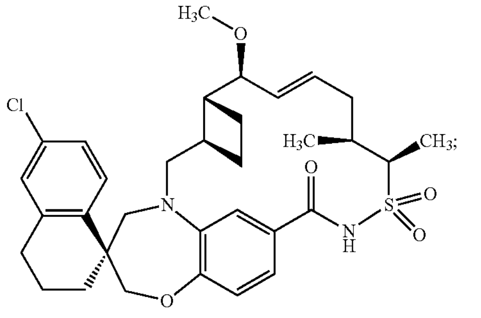

b) a cyclodextrin compound;
c) a buffer; and
d) water, wherein, the concentration of the compound of Formula I or the salt thereof in the formulation ranges from 15 mg/mL to 30 mg/mL and the pH of the formulation ranges from 8.7 to 9.9. Preferably, the method comprises administering the formulation intravenously, and preferably the method comprises diluting the formulation, e.g. in a bag containing saline, prior to intravenous administration. The method may optionally further comprise administering a second therapeutic agent selected from the list consisting of venetoclax, carfilzomib, azacitidine, and dexamethasone.

The invention provides an aqueous solution for use in a method of treating cancer in a patient, wherein the aqueous solution comprises:

(a) the compound of Formula I or a salt of the compound of Formula I, wherein the compound of Formula I has the following structure:

I

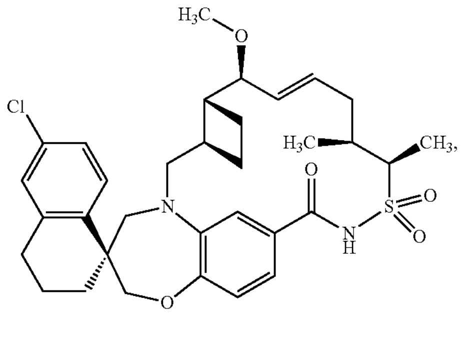

(b) a cyclodextrin compound;
(c) a buffer;
(d) sodium chloride; and
(e) water:

wherein the amount of the compound of Formula I or a salt of the compound of Formula I in the solution ranges from 25 mg to 400 mg. Preferably the cancer is a hematological malignancy, and most preferably the cancer is selected from the list consisting of acute myelogenous leukemia, multiple myeloma, or non-Hodgkin's lymphoma. Preferably, the method comprises administering the solution intravenously, and preferably the method comprises a dilution step, e.g. into a bag containing saline, prior to intravenous administration. The method may optionally further comprise administering a second therapeutic agent selected from the list consisting of venetoclax, carfilzomib, azacitidine, and dexamethasone.

The invention provides an aqueous solution for use in a method of treating cancer, wherein the aqueous solution comprises:

(a) the compound of Formula I or a salt of the compound of Formula I, wherein the compound of Formula I has the following structure:

I

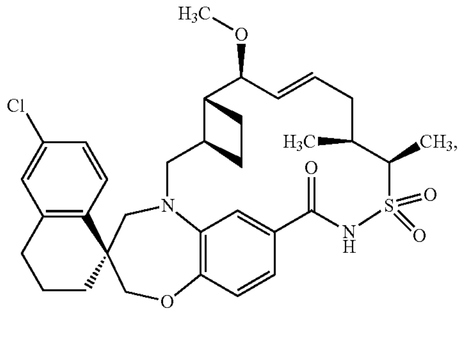

(b) a cyclodextrin compound;
(c) a buffer;
(d) sodium chloride; and
(e) water:

wherein the amount of the compound of Formula I or a salt of the compound of Formula I in the solution ranges from 25 mg to 400 mg;

wherein the method comprises administering the compound of Formula I or the salt of the compound of Formula I in an amount ranging from 25 $mg/m^2$ to 960 $mg/m^2$. Preferably the cancer is a hematological malignancy, and most preferably the cancer is selected from the list consisting of acute myelogenous leukemia, multiple myeloma, or non-Hodgkin's lymphoma. Preferably, the method comprises administering the solution intravenously, and preferably the method comprises a dilution step, e.g. into a bag containing saline, prior to intravenous administration. The method may optionally further comprise administering a second therapeutic agent selected from the list consisting of venetoclax, carfilzomib, azacitidine, and dexamethasone.

The invention provides a pharmaceutical formulation for use in a method of treating cancer, wherein the pharmaceutical formulation comprises:

a) a compound of Formula I or a salt thereof, wherein the compound of Formula I has the following structure:

I

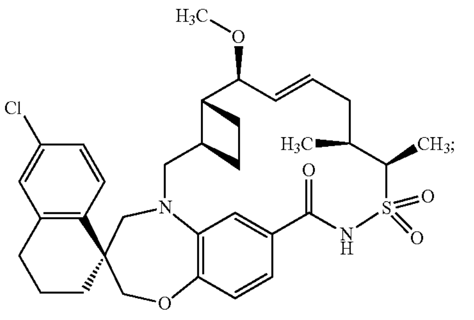

b) a cyclodextrin compound;

c) a buffer; and d) water, wherein the concentration of the compound of Formula I or the salt thereof in the formulation ranges from 15 mg/mL to 30 mg/mL and the pH of the formulation ranges from 8.7 to 9.9. Preferably the cancer is a hematological malignancy, and most preferably the cancer is selected from the list consisting of acute myelogenous leukemia, multiple myeloma, or non-Hodgkin's lymphoma. Preferably, the method comprises administering the formulation intravenously, and preferably the method comprises diluting the formulation, e.g. in a bag containing saline, prior to intravenous administration. The method may optionally further comprise administering a second therapeutic agent selected from the list consisting of venetoclax, carfilzomib, azacitidine, and dexamethasone.

The invention provides a pharmaceutical formulation for use in a method of treating cancer, wherein the pharmaceutical formulation comprises:

a) a compound of Formula I or a salt thereof, wherein the compound of Formula I has the following structure:

I

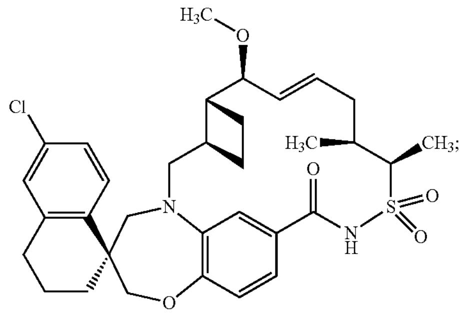

b) a cyclodextrin compound;

c) a buffer; and d) water, wherein, the concentration of the compound of Formula I or the salt thereof in the formulation ranges from 15 mg/mL to 30 mg/mL and the pH of the formulation ranges from 8.7 to 9.9;

wherein the method comprises administering the compound of Formula I or the salt of the compound of Formula I in an amount ranging from 25 $mg/m^2$ to 960 $mg/m^2$. Preferably the cancer is a hematological malignancy, and most preferably the cancer is selected from the list consisting of acute myelogenous leukemia, multiple myeloma, or non-Hodgkin's lymphoma. Preferably, the method comprises administering the formulation intravenously, and preferably the method comprises diluting the formulation, e.g. in a bag containing saline, prior to intravenous administration. The method may optionally further comprise administering a second therapeutic agent selected from the list consisting of venetoclax, carfilzomib, azacitidine, and dexamethasone.

The invention provides an aqueous solution for use in a method of treating cancer in a patient, wherein the aqueous solution comprises the compound of Formula I or a salt of the compound of Formula I, wherein the compound of Formula I has the following structure:

I

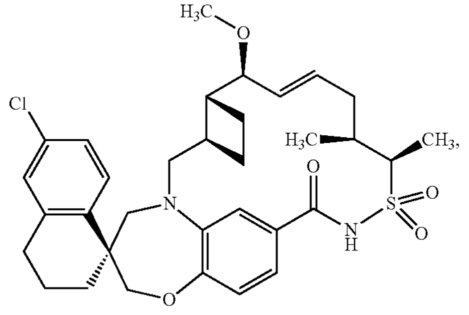

wherein the method comprises administering the compound of Formula I or the salt of the compound of Formula I in an amount ranging from 25 $mg/m^2$ to 960 $mg/m^2$; wherein the method further comprises administering a second therapeutic agent selected from the list consisting of venetoclax, carfilzomib, azacitidine, and dexamethasone. Preferably the cancer is a hematological malignancy, and most preferably the cancer is selected from the list consisting of acute myelogenous leukemia, multiple myeloma, or non-Hodgkin's lymphoma. Optionally, the method may comprise administering the pharmaceutical formulation of any of embodiments 1-30 or the aqueous solution of any of embodiments 33-36.

The invention provides an aqueous solution for use in a method of treating acute myelogenous leukemia in a patient, wherein the aqueous solution comprises the compound of Formula I or a salt of the compound of Formula I, wherein the compound of Formula I has the following structure:

I

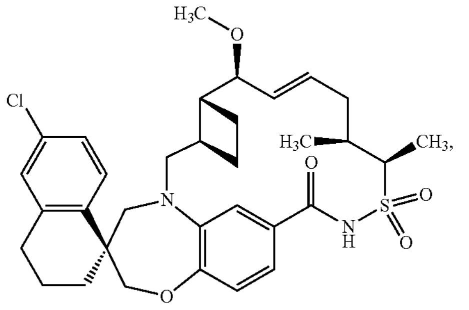

wherein the method comprises administering the compound of Formula I or the salt of the compound of Formula I in an amount ranging from 25 $mg/m^2$ to 960 $mg/m^2$. Preferably, the method comprises administering the aqueous solution intravenously. The method may optionally further comprise administering a second therapeutic agent selected from the list consisting of venetoclax, carfilzomib, azacitidine, and dexamethasone.

The invention provides an aqueous solution for use in a method of treating multiple myeloma in a patient, wherein the aqueous solution comprises the compound of Formula I or a salt of the compound of Formula I, wherein the compound of Formula I has the following structure:

I

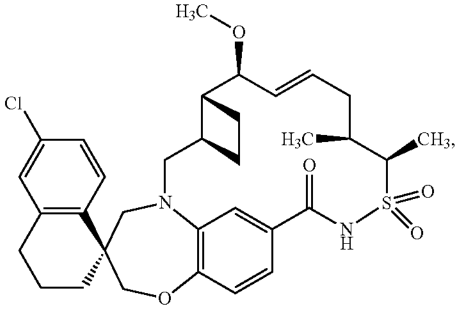

wherein the method comprises administering the compound of Formula I or the salt of the compound of Formula I in an amount ranging from 25 $mg/m^2$ to 960 $mg/m^2$. Preferably, the method comprises administering the aqueous solution intravenously. The method may optionally further comprise administering a second therapeutic agent selected from the list consisting of venetoclax, carfilzomib, azacitidine, and dexamethasone.

The invention provides an aqueous solution for use in a method of treating non-Hodgkin's lymphoma in a patient, wherein the aqueous solution comprises the compound of Formula I or a salt of the compound of Formula I, wherein the compound of Formula I has the following structure:

I

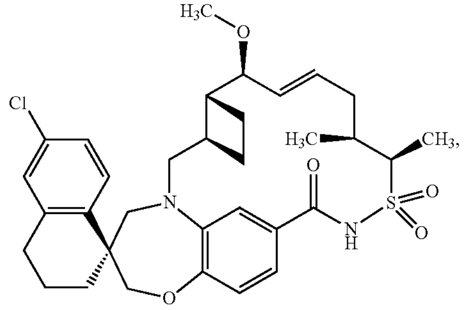

wherein the method comprises administering the compound of Formula I or the salt of the compound of Formula I in an amount ranging from 25 $mg/m^2$ to 960 $mg/m^2$. Preferably, the method comprises administering the aqueous solution intravenously. The method may optionally further comprise administering a second therapeutic agent selected from the list consisting of venetoclax, carfilzomib, azacitidine, and dexamethasone.

The invention provides an aqueous solution for use in a method of treating multiple myeloma, wherein the aqueous solution comprises the compound of Formula I or a salt of the compound of Formula I, wherein the compound of Formula I has the following structure:

I

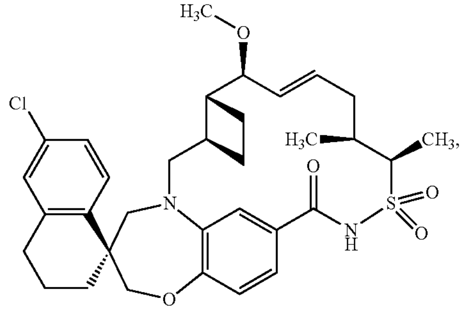

wherein the method comprises administering the compound of Formula I or the salt of the compound of Formula I in an amount ranging from 25 $mg/m^2$ to 960 $mg/m^2$ wherein the method further comprises administering carfilzomib as a second therapeutic agent. Preferably, the method comprises administering the solution intravenously.

The invention provides a therapeutic agent selected from the list consisting of venetoclax, carfilzomib, azacitidine, and dexamethasone for use in a method of treating cancer in a patient, wherein the method comprises administering said therapeutic agent to the patient and further comprises administering to the patient aqueous solution comprises the compound of Formula I or a salt of the compound of Formula I, wherein the compound of Formula I has the following structure:

I

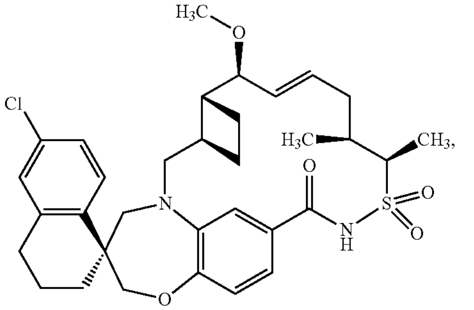

wherein the method comprises administering the compound of Formula I or the salt of the compound of Formula I in an amount ranging from 25 mg/m$^2$ to 960 mg/m$^2$. Preferably the cancer is a hematological malignancy, and most preferably the cancer is selected from the list consisting of acute myelogenous leukemia, multiple myeloma, or non-Hodgkin's lymphoma. Preferably, the method comprises administering the solution intravenously. Optionally, the method may comprise administering the pharmaceutical formulation of any of embodiments 1-30 or the aqueous solution of any of embodiments 33-36.

The invention provides any of the formulations disclosed herein for use in a method of treating cancer in a patient. It goes without saying that preferably the patient is a human and preferably the cancers to which the invention is directed are human cancers. Preferably, the method comprises administering the formulation intravenously.

The invention further provides any of the formulations disclosed herein for use in a method of treating acute myelogenous leukemia, multiple myeloma, or non-Hodgkin's lymphoma in a patient.

The invention further provides the pharmaceutical composition of embodiment 1 above for use in a method of treating acute myelogenous leukemia, multiple myeloma, or non-Hodgkin's lymphoma.

The invention further provides the aqueous solution of embodiment 33 above for use in a method of treating acute myelogenous leukemia, multiple myeloma, or non-Hodgkin's lymphoma.

The invention provides any of the formulations disclosed herein for use in a method of treating cancer in a patient, wherein said method further comprises administering a second therapeutic agent selected from the list consisting of venetoclax, carfilzomib, azacitidine, and dexamethasone. Preferably, the formulation comprising the compound of Formula I or a salt thereof is administered intravenously.

The invention further provides any of the formulations disclosed herein for use in a method of treating acute myelogenous leukemia, multiple myeloma, or non-Hodgkin's lymphoma comprising administering to the patient any of the formulations disclosed herein and a second therapeutic agent selected from the list consisting of venetoclax, carfilzomib, azacitidine, and dexamethasone.

The invention further provides the pharmaceutical composition of embodiment 1 above for use in a method of treating acute myelogenous leukemia, multiple myeloma, or non-Hodgkin's lymphoma in a patient, comprising administering to the patient the pharmaceutical composition of embodiment 1 above and a second therapeutic agent selected from the list consisting of venetoclax, carfilzomib, azacitidine, and dexamethasone. Preferably, the pharmaceutical composition is administered intravenously. Optionally, the method comprises administering the compound of Formula I or the salt of the compound of Formula I in an amount ranging from 25 mg/m$^2$ to 960 mg/m$^2$.

The invention further provides the pharmaceutical composition of embodiment 1 above for use in a method of treating multiple myeloma in a patient, comprising administering to the patient the pharmaceutical composition of embodiment 1 above and carfilzomib as a second therapeutic agent. Preferably, the pharmaceutical composition is administered intravenously. Optionally, the method comprises administering the compound of Formula I or the salt of the compound of Formula I in an amount ranging from 25 mg/m$^2$ to 960 mg/m$^2$.

The invention further provides the aqueous solution of embodiment 33 above for use in a method of treating acute myelogenous leukemia, multiple myeloma, or non-Hodgkin's lymphoma in a patient comprising administering to the patient the aqueous solution of embodiment 33 above and a second therapeutic agent selected from the list consisting of venetoclax, carfilzomib, azacitidine, and dexamethasone. Preferably, the aqueous solution is administered intravenously. Optionally, the method comprises administering the compound of Formula I or the salt of the compound of Formula I in an amount ranging from 25 mg/m$^2$ to 960 mg/m$^2$.

The invention further provides the aqueous solution of embodiment 33 above for use in a method of treating multiple myeloma in a patient comprising administering to the patient the aqueous solution of embodiment 33 above and carfilzomib as a second therapeutic agent. Preferably, the aqueous solution is administered intravenously. Optionally, the method comprises administering the compound of Formula I or the salt of the compound of Formula I in an amount ranging from 25 mg/m$^2$ to 960 mg/m$^2$.

The invention provides a vial comprising the pharmaceutical formulation of any one of embodiments 1-30 above.

The invention further provides a vial comprising the pharmaceutical formulation of any one of embodiments 1-30 above, wherein the vial is a 20 mL borosilicate glass vial or a 20 mL aluminosilicate glass vial, wherein the vial is equipped with a stopper and an aluminum seal with a flip off cover.

The invention further provides a vial comprising the aqueous solution of any one of embodiments 33-36 above.

The invention further provides an IV bag comprising the aqueous solution of any one of embodiments 33-36 above.

The invention further provides an IV bag comprising the pharmaceutical formulation of any one of embodiments 1-30 above. In a preferred embodiment, the solution within the IV bag is diluted relative to the formulation that is transferred into the IV bag, e.g. because the solution within the IV bag additionally comprises saline which is not present in the formulation that is transferred into the IV bag.

In one embodiment the medical uses or methods of treatment disclosed herein result in one or more of the following:

- At least 1000-fold, preferably 2000-fold, more preferably 3000-fold and most preferably 4000-fold selectivity for MCL1 over BCL2 and/or BCL-XL; and
- Achievement of stable disease, and more preferably partial remission, and most preferably complete remission. This second bullet point applies preferably in relation to the treatment of AML—see the example below.

The combination therapies disclosed herein may be administered simultaneously, separately and sequentially, in any order. Thus, and purely by way of example, the invention relates to venetoclax, carfilzomib, azacitidine, and/or dexamethasone for use in a method of treating cancer when administered in combination with any of the AMG 176 embodiments (solutions and formulations etc.) disclosed herein. In an alternative embodiment, the invention relates any of the AMG 176 embodiments (solutions and formulations etc.) for use in a method of treating cancer when administered in combination with venetoclax, carfilzomib, azacitidine, and/or dexamethasone. Preferably any such combination therapy exceeds the effect achieved with one of the constituent single agents administered alone (or if the combination therapy involves greater than two agents, preferably the combination exceeds the effect achieved with one of the constituent single agents administered alone and any of the constituent sub-combinations making up the combination therapy).

The invention is further described by reference to the following examples, which are intended to exemplify the claimed invention but not to limit it in any way.

EXAMPLES

The compound of Formula I is a selective small molecule inhibitor of protein-protein interactions between MCL1 and pro-apoptotic members of the BCL2 family that is being investigated in the treatment of patients with cancer, and in particular in patients with hematological malignancies including, but not limited to multiple myeloma and acute myelogenous leukemia (Caenepeel et al, Cancer Discov 8:1582-1597 (2018)).

The compound of Formula I and salts of the compound of Formula I are compounds that inhibit MC11 protein. The structure of the compound of Formula I is shown below:

I

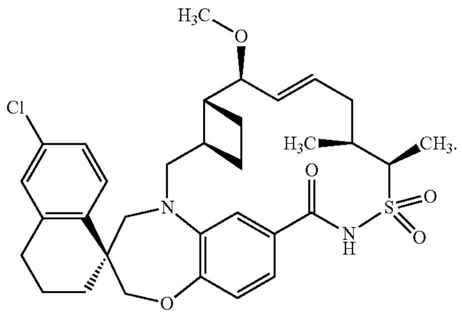

The compound of Formula I is also referred to as AMG 176. Compounds of Formula I and salts thereof and methods for synthesizing the compound are described in WO 2016/033486 and U.S. Pat. No. 9,562,061. These references are incorporated by reference herein in their entireties as if specifically set forth.

Nonclinical Studies—Pharmacology

In vitro, the compound of Formula I selectively disrupts the human MCL1-BIM interaction in a time-resolved fluorescence resonance energy transfer-based assay, with a mean half-maximal inhibitory concentration ($IC_{50}$) of 0.241 nM (Table 1). Furthermore, the compound is highly selective for MCL1, demonstrating greater than 4000 fold selectivity over the pro-survival BCL2 family members, BCL2 and B-cell lymphoma/leukemia-extra large (BCL-XL). In cellular assays, the compound of Formula I disrupts the interaction between MCL1 and BAK with a mean $IC_{50}$ of 30.8 nM. In cell viability studies performed in a panel of tumor cell lines derived from multiple myeloma, acute myelogenous leukemia, and non-Hodgkin's lymphoma, the compound exhibited $IC_{50}$ values ranging from 14 nM to greater than 20 μM, with $IC_{50}$ values of less than 1 μM observed in 12 of the 23 tested cell lines.

TABLE 1

AMG 176 Binding Activity and Selectivity Profile in Cell-free Time-resolve Fluorescence Resonance Energy Transfer BIM-binding Assay

| BIM-Binding Partner | $IC_{50}$ (Mean ± SD) of AMG 176 With Respect to Binding (nM) |
|---|---|
| Human MCL1 | 0.241 ± 0.048 (n = 7) |
| Dog MCL1 | 0.284 ± 0.035 (n = 3) |
| Monkey MCL1 | 0.182 ± 0.017 (n = 3) |
| Rabbit MCL1 | 0.191 ± 0.011 (n = 3) |
| Mouse MCL1 | 49.8 ± 8.8 (n = 3) |
| Human BCL2 | 1123 ± 125 (n = 3) |
| Human BCL-XL | 1187 ± 140 (n = 3) |

BCL2 = B-cell lymphoma 2;
BCL-XL = B-cell lymphoma/leukemia-extra large;
BIM = BCL2-interacting mediator of cell death;
$IC_{50}$ = half-maximal inhibitory concentration;
MCL1 = myeioid cell leukemia 1

In vivo, treatment with the compound of Formula I resulted in a dose-dependent inhibition of the interaction between human MCL1 and human BAK. Treatment with the compound also resulted in dose-dependent induction of multiple markers of apoptosis, including BAK activation and caspase 3 cleavage in tumor xenografts from a human MCL1 dependent multiple myeloma cell line stably transduced with the luciferase gene (OPM2-Luc). In an OPM2-Luc xenograft efficacy model, treatment with the compound of Formula I significantly inhibited the growth of established tumors, with tumor regression observed at 2 dosages, 30 mg/kg and 60 mg/kg administered orally once daily. Additional studies examining the efficacy of the compound of Formula I were performed in an OPM2-Luc tumor xenograft model using intermittent dosing schedules. The compound of Formula I significantly inhibited the growth of established tumors at doses of 30 mg/kg and 60 mg/kg with two days on/5 days off and 5 days on/2 days off schedules. Once-weekly oral administration of AMG 176 doses of 50 and 100 mg/kg resulted in tumor growth inhibition (TGI) of 97% and 70% respectively. The efficacy of the compound of Formula I was also assessed in the MOLM13 luciferase-labeled orthotopic model of acute myelogenous leukemia in which MOLM13 tumor cells have engrafted into the bone marrow of mice. In this model, oral administration of the compound at 30 mg/kg or 60 mg/kg on a schedule of 2 days on/5 days off (QD2) resulted in significant dose-dependent inhibition of tumor burden as assessed by whole body luminescence (28% and 69% TGI, respectively) and once-daily oral administration of the compound at 100 mg/kg resulted in 86% TGI. The therapeutic potential of the combination of the compound of Formula I and the proteasome inhibitor carfilzomib was tested in an orthotopic OPM2-Luc model. In mice treated once daily with the compound (20 mg/kg) and twice weekly with carfilzomib (3 mg/kg), the combination achieved significant inhibition of tumor burden (99% TGI), exceeding the effect achieved with either single agent alone (86% TGI with the compound of Formula I and 82% TGI with carfilzomib).

In a study with HEK 293M cells transiently transfected with MCL1 and BAK, AMG 176 inhibited the interaction between MCL1 and BAK with a mean $IC_{50}$ of 30.8 nM in serum-free growth medium. AMG 176 inhibited the viability of the OPM2 multiple myeloma tumor cell line in a dose-dependent manner, with $IC_{50}$ values of 15.5 nM (serum-free growth medium), 235.7 nM (growth medium containing 10% fetal bovine serum [FBS]) and 703.4 nM (growth medium containing 5% human serum). In additional tumor cell viability studies, performed in growth medium containing 10% FBS, AMG 176 exhibited IC50 values of less than 1 μM in 12 of 23 tumor cell lines derived from multiple myeloma, AML, and NHL (Table 2).

TABLE 2

AMG 176 $IC_{50}$ Values From Viability Studies Performed With AML, Multiple Myeloma, and NHL Tumor Cell Lines.

| Cell Line | Tumor Type | AMS 176 $IC_{50}$ (μM) |
|---|---|---|
| KMS-12-BM | Multiple myeloma | 0.015 |
| Ramos | NHL | 0.034 |
| HL-60 | AML | 0.110 |
| KMS-12-PE | Multiple myeloma | 0.131 |
| SU-OHL-6 | NHL | 0.165 |
| KMS-28-BM | Multiple myeloma | 0.205 |
| Namalwa | NHL | 0.237 |
| MOLM-13 | AML | 0.241 |
| KMS26 | Multiple myeloma | 0.248 |
| KMM1 | Multiple myeloma | 0.407 |
| U937 | NHL | 0.474 |
| Karoas620 | Multiple myeloma | 0.487 |
| MM1R | Multiple myeloma | 1.138 |
| TF-1 | AML | 2.093 |
| Raji | NHL | 3.551 |
| MM1S | Multiple myeloma | 5.115 |
| HEL 92.1.7 | AML | 5.989 |
| KMS34 | Multiple myeloma | 6.050 |
| U26681 | Multiple myeloma | 8.220 |
| Toledo | NHL | 9.697 |
| KMS-28-PE | Multiple myeloma | 12.005 |
| Pfeiffer | NHL | 18.865 |
| RL | NHL | >20 |

AML = acute myeloid leukemia;
$IC_{50}$ = half-maximal inhibitory concentration;
NHL = non-Hodgkin lymphoma
Cell lines were treated with serially diluted AMG 176 with a high dose of 20 μM for 24 hours. Cell viability was determined using a CellTiterGlo ® luminescent cell viability assay. Depicted are the mean $IC_{50}$ values from 2 or 3 independent experiments.

Inhibition by AMG 176 of MCL1-BAK Protein-Protein Interaction in a HEK 293M Matrigel™ Plug Model The inhibition of MCL1-BAK protein-protein interaction was used as a pharmacodynamics (PD) assay in HEK 293M cells stably transfected so as to express the N-terminal fragment of human MCL1 encoding amino acids 1-327 and full-length human BAK, linked to the N- and C-terminal fragments of firefly luciferase, respectively (interaction between MCL1 [1-327] and BAK results in the complementation of the C- and N-terminal fragments of luciferase and the formation of active luciferase). The effects of AMG 176 on MCL1-BAK protein-protein interaction as functions of both dose and time were evaluated in Matrigel™ plugs containing the human HEK 293M MCL1 (1-327) Luc/BAK-Luc cells implanted in female athymic nude mice; AMG 176 significantly inhibited MCL1-BAK protein-protein interaction, as measured by luciferase activity (FIG. 1). Statistically significant inhibition was seen with 3 mg/kg AMG 176 (2-, 8-, 12-, and 24-hour time points), 10 mg/kg AMG 176 (2-, 4-, 8-, and 12-hour time points), and 30 mg/kg AMG 176 (2-, 4-, 8-, 12-, and 24-hour time points) when compared with the vehicle control group ($p<0.0025$, (FIG. 1)).

Induction by AMG 176 of Multiple Hallmarks of Apoptosis, Including BAK Activation an Caspase 3 Cleavage, in OPM2-Luc Tumor Xenografts Activation of the pro-apoptotic pore-forming protein BAK and proteolytic cleavage of the cysteine-aspartic acid protease caspase 3 (hallmarks of the induction of apoptosis) in MCL1-dependent OPM2-Luc multiple myeloma tumor cells served as a PD assay. Female athymic nude mice were injected with $5\times10^6$ cells in 0.1 mL subcutaneously (SC). When tumors reached volumes ranging from approximately 400 to 600 $mm^3$, AMG 176 was administered by oral gavage at doses of 10, 20, 30, or 60 mg/kg. Mice were euthanized 2, 4, 8, 12, and 24 hours postdose (n=3/group), terminal plasma samples were collected for PK analysis, and tumors were halved and snap frozen in liquid nitrogen for PK and molecular analyses. Tumor lysates were prepared for evaluation of BAK activation and caspase 3 cleavage using an electrochemiluminescence immunoassay. Tumors treated with vehicle (25% HPβCD, pH 8) served as a negative control and indicated the baseline level of apoptosis. Statistically significant BAK activation was observed at doses of 30 mg/kg (2-, 4-, and 8-hour time points) and 60 mg/kg (2-, 4-, 8-, and 12-hour time points) when compared with the vehicle control group ($p<0.05$ [FIG. 2]). The greatest BAK activation was observed in the 60 mg/kg group at the 4-hour time point, corresponding with the peak AMG 176 plasma concentration. FIG. 3 shows induction of caspase 3 cleavage and the corresponding concentrations of AMG 176 in plasma and tumors. Statistically significant induction of caspase 3 cleavage was observed at doses of 20 mg/kg (4-, 8-, and 12-hour time points), 30 mg/kg (2-, 4-, 8-, and 12-hour time points), and 60 mg/kg (2-, 4-, 8-, 12-, and 24-hour time points) when compared with the vehicle control group ($p<0.05$, [FIG. 2]). At 2 hours postdose, an approximately 7.5-fold induction of cleaved caspase 3 was observed in the 60 mg/kg group, which persisted to 12 hours postdose. By 24 hours postdose, cleaved caspase levels had declined to 5-fold above control, corresponding with reduced AMG 176 plasma concentration.

AMG 176 Inhibited the Growth of OPM2-Luc Tumor Xenografts as a Single Agent

AMG 176 was evaluated for its ability to inhibit tumor growth in the MCL1-dependent OPM2 multiple myeloma xenograft model. OPM2-Luc cells ($5\times10^6$) were implanted subcutaneously into female athymic nude mice. Treatment with vehicle or AMG 176 at 10, 20, 30, or 60 mg/kg, once daily by oral gavage, began on day 14 when tumor volumes reached approximately 150 $mm^3$ (n=10/group). Dose-dependent TGI was observed, and AMG 176 statistically significantly inhibited the growth of OPM2-Luc tumors at doses 20, 30, and 60 mg/kg ($p<0.001$ compared with vehicle control group) (FIG. 4). The 20 mg/kg group showed 63% TGI ($p<0.001$ compared with the vehicle control group). The 30 and 60 mg/kg groups showed statistically significant tumor regression (50% regression and 100% regression, respectively; $p<0.001$ and $p<0.0001$, respectively) compared with the vehicle control group. Three of 10 animals in the 30 mg/kg group and 10 of 10 animals in the 60 mg/kg group were tumor free on day 24. There was no evidence of AMG 176-related changes in body weight and body score assessment; however, it should be noted that AMG 176 is less potent against mouse MCL1 than against human MCL1.

In a separate study, AMG 176 was tested for its ability to inhibit tumor growth in the OPM2-Luc multiple myeloma xenograft model with various intermittent-dosing schedules. OPM2-Luc cells ($5\times10^6$) were implanted subcutaneously into female athymic nude mice. Treatment began on day 14 by oral gavage with vehicle once daily or AMG 176 at doses of 30 or 60 mg/kg once daily (QD), 5 days on/2 days off (5×/week, QD5), or 2 days on/5 days off (2×/week, QD2) when tumor volumes had reached approximately 150 $mm^3$ (n=10/group). With all tested doses and schedules, dose-dependent TGI was observed (FIG. 5). At the 30-mg/kg dose, 84% TGI was observed with once daily dosing ($p<0.001$ compared with vehicle control group), 85% TGI was observed with 5 days on/2 days off ($p<0.001$), and 54% TGI was observed with 2 days on/5 days off ($p<0.001$). At the 60-mg/kg dose, 100% tumor regression was observed with once daily dosing, 87% tumor regression was observed with 5 days on/2 days off, and 21% tumor regression was observed with 2 days on/5 days off ($p<0.001$). Six of 10 animals in the 60 mg/kg 5 days on/2 days off group and 10 of 10 animals in the once daily group were tumor free on day 26. No evidence of overt toxicity was observed in the AMG 176-treated groups as determined by changes in body weight and body score assessment; however, as noted above, AMG 176 is less potent against mouse MCL1 than against human MCL1.

The Effect of Once-Weekly Dosing of AMG 176 on Tumor Growth in the OPM2-Luc Xenograft in Female Athymic Nude Mice AMG 176 was tested for its ability to inhibit tumor growth in the OPM2 multiple myeloma xenograft model using a once-weekly dosing schedule. Female athymic nude mice were injected subcutaneously with $5\times10^6$ human OPM2-Luc multiple myeloma tumor cells. Treatment began on day 15 with vehicle or AMG 176 at doses of 50 or 100 mg/kg orally once per week and 50 mg/kg intraperitoneally once per week, when tumor volume reached an average of 120 to 206 $mm^3$. Tumor volume and body weight were measured twice per week through day 26. AMG 176 significantly inhibited the growth of OPM2-Luc tumors. In the 50 mg/kg oral group, 97% TGI ($p<0.0001$) was observed; in the 100 mg/kg group, 70% regression was observed ($p<0.0001$). In the 50 mg/kg intraperitoneal group, 98% regression was observed ($p<0.0001$) (FIG. 6). Five out of 10 animals in the 100 mg/kg group were tumor free at day 26. No evidence of overt toxicity was observed in the AMG 176 treated groups as determined by changes in body weight.

In Vivo Activity of AMG 176 in the MOLM-13 Luc Acute Myeloid Leukemia Orthotopic Model in Female NSG Mice AMG 176 was evaluated to explore its ability to inhibit the growth of established Molm13-Luc orthotopic tumors in female NOD/SCID IL2rg (NSG) mice. On day 0, 70 female NSG mice were injected IV with $5\times10^4$ human Molm13-Luc AML tumor cells. After randomization into 4 groups (n=10/group), oral treatment with AMG 176 beginning on day 7 resulted in significant TGI of orthotopic Molm13-Luc tumors. In a QD2 treatment schedule, 30 mg/kg of AMG 176 resulted in 28% TGI compared with the vehicle control group ($p<0.0001$), and 60 mg/kg of AMG 176 resulted in 69% TGI ($p<0.0001$); treatment with AMG 176 at 100 mg/kg QD resulted in 86% TGI ($p<0.0001$) (FIG. 7). No evidence of overt toxicity was observed in the AMG 176 treated groups as determined by changes in body weight.

In Vivo Activity of AMG 176 Plus Carfilzomib in the OPM2-Luc Multiple Myeloma Orthotopic Model AMG 176 has previously demonstrated the ability to induce statistically significant TGI as a single agent in the OPM2-Luc multiple myeloma model. This study investigated the potential for the combination of AMG 176 and carfilzomib to inhibit tumor growth in the OPM2-Luc orthotopic model. On day 0, female NSG mice were injected IV with $1\times10^6$ OPM2-Luc human OPM2-Luc multiple myeloma tumor cells transfected with the firefly luciferase gene. After randomization into 4 groups (n=10/group), mice were treated orally once daily with vehicle or with AMG 176 at 20 mg/kg and treated IV with either vehicle or carfilzomib at 3 mg/kg twice weekly from day 4 until day 20. In mice treated once daily with AMG 176 (20 mg/kg) and twice weekly with carfilzomib (3 mg/kg), the combination achieved statistically significant inhibition of tumor burden (99% TGI, $p<0.0001$ versus carfilzomib alone), exceeding the effect achieved with either single agent (86% and 82% TGI with AMG 176 or carfilzomib, respectively) (FIG. 8). Unscheduled deaths in the carfilzomib monotherapy and the combination group were observed, implicating a lack of tolerability of IV carfilzomib in NSG mice.

Nonclinical Studies—Pharmacokinetics

The pharmacokinetics (PK) of the compound of Formula I after single intravenous (IV) or oral administration were characterized in male CD1 mice, female athymic nude mice, male Nu/Nu mice, male Sprague Dawley rats, male beagle dogs, and male cynomolgus monkeys. The clearance (CL) of the compound was low in mice, rats, dogs, and monkeys relative to their hepatic blood flow. Volume of distribution at steady state ($V_{ss}$) in mice, rats, dogs, and monkeys was variable across the species. The mean terminal elimination half-life ($t_{1/2,z}$) values in mice, rats, dogs, and monkeys were 13.8, 19.5, 10.8, and 1.66 hours respectively. The compound of Formula I was highly plasma-protein bound in vitro, and did not preferentially distribute into blood cells.

Nonclinical Studies—Toxicology

Nonclinical safety studies on the compound of Formula I consisted of an exploratory 14-day dog IV toxicology study, Good Laboratory Practices (GLP) 28-day rat and dog IV toxicology studies, in vitro exploratory genotoxicity studies (GLP human ether-á-go-go related gene [hERG] and non-GLP isolated rabbit heart) to characterize potential cardiovascular effects. The doses selected for the 28-day IV rat and dog toxicology studies were intended to characterize the toxicity of the compound of Formula I and provide data to support a starting dose in the first-in-human (FIH) study. An IV route of administration and a dosing schedule of 2 days on/5 days off was used to support the anticipated clinical route and dosing schedule. In a 28-day GLP rat IV infusion toxicology study, the severely toxic dose in 10% of animals ($STD_{10}$) was 60 mg/kg based on mortality at 120 mg/kg and in a 28-day GLP IV toxicology study in dogs, the highest-nonseverely-toxic dose (HNSTD) was 10 mg/kg based on mortality at 20 mg/kg. In both the rat and dog, morbidity and mortality was related to mucosal epithelial degeneration in the small and large intestines. The compound of Formula I was not mutagenic or clastogenic in exploratory in vitro genotoxicity studies. The compound was also not phototoxic in an in vivo phototoxicity study. In vehicles containing hydroxypropyl-β-cyclodextrin, the compound of Formula I cased hemolysis (in vitro) of whole blood at concentrations of 0.048, 0.12, 0.24, 1.2, and 2.4 mg/mL in rat blood and at 0.1 and 1.0 mg/mL in dog blood, but was not hemolytic in human blood at the highest concentration tested, 0.25 mg/mL.

Effects in Humans

The compound of Formula I is and has been investigated in a phase 1, FIH, multicenter, nonrandomized, open-label, dose-exploration study in subjects with relapsed/refractory multiple myeloma and in subjects with relapsed/refractory acute myelogenous leukemia. Preliminary data was available for 32 subjects with multiple myeloma and for 10 subjects with AML.

Multiple Myeloma

A total of 32 subjects were enrolled and had received at least 1 dose of the compound of Formula I; 26 subjects in part 1a (once daily for 2 consecutive days followed by a 5-day break [QD2]) and 6 subjects in part 1b (once-weekly [QW]). In part 1a, subjects were enrolled across 8 cohorts, with doses ranging from 30 to 240 $mg/m^2$ QD2. In part 1b, subjects were enrolled across 2 cohorts, with doses of 120/180-$mg/m^2$ or 120/240-$mg/m^2$.

Preliminary PK data were available from 25 subjects in part 1a and 6 subjects in part 1b. AMG 176 exposures (maximum observed drug concentration [$C_{max}$] and area under the concentration-time curve [AUC]) generally increased with increasing doses across the dose ranges studied.

In part 1a, treatment-emergent adverse events were reported in 25 subjects (96%); the most frequently reported events (≥20% of subjects) were nausea (35%), neutropenia and diarrhea (31% each), and fatigue and anemia (27% each). Grade 3 adverse events occurred in 17 subjects (65%) and grade 4 adverse events occurred in 8 subjects (31%); adverse events of grade 3 or higher reported in >1 subject were neutropenia (31%), anemia (15%), and decreased white blood cell count, hypertension, and decreased neutrophil count (8% each). Serious adverse events were reported in 8 subjects (31%); by preferred term, no serious adverse event occurred in >1 subject. No adverse event led to discontinuation of investigational product. Two fatal adverse events occurred. The fatal event of hepatic failure occurred in a subject in the 50 mg/$m^2$ cohort, this event occurred in the context of disease progression and was considered by the investigator as not related to AMG 176. The fatal event of tumor lysis syndrome occurred in 1 subject in the 240 mg/$m^2$ cohort; this event was considered by the investigator as related to AMG 176 and was also the only dose-limiting toxicity (DLT) reported. Adverse events considered by the investigator as related to AMG 176 treatment were reported in 18 subjects (69%); by preferred term, the most frequently reported events (≥15% of subjects) were neutropenia (23%), nausea (23%), and diarrhea (19%).

In part 1b, adverse events were reported in 5 subjects (83%); the most frequently reported events (occurring in >1 subject) were neutropenia (67%), nausea (50%), and diarrhea, fatigue, and hypertension (33% each). Grade 3 adverse events occurred in 5 subjects (83%) and grade 4 adverse events occurred in 1 subject (17%); adverse events of grade 3 or higher reported in >1 subject were neutropenia (67%) and hypertension (33%). No serious adverse events were reported, no adverse event led to discontinuation of investigational product, and no fatal adverse events occurred. Adverse events considered by the investigator as related to AMG 176 treatment were reported in 5 subjects (83%/a); by preferred term, the most frequently reported events (≥30% of Acute Myeloid Leukemia In part 3, 10 total subjects were enrolled across 2 cohorts, with doses of 60 mg/$m^2$ or 120 mg/$m^2$.

Preliminary PK data were available from 10 subjects with AML. AMG 176 exposures ($C_{max}$ and AUC) generally increased with increasing doses across the dose ranges studied.

Adverse events were reported in 8 subjects (80%); the most frequently reported events (occurring in >1 subject) were hypokalemia, peripheral edema, and nausea (30% each), and increased blood bilirubin, hypomagnesemia, anemia, pyrexia, and vomiting (20% each). Grade 3 adverse events occurred in 7 subjects (70%) and grade 4 adverse events occurred in 2 subjects (20%); the only adverse event of grade 3 or higher reported in >1 subject for both cohorts combined was anemia (20%). Serious adverse events were reported in 6 subjects (60%); by preferred term, no serious adverse events occurred in >1 subject. Adverse events led to discontinuation of investigational product in 2 subjects (20%); by preferred term, superior vena cava syndrome and febrile neutropenia were each reported in 10% of subjects. No fatal adverse events occurred. Adverse events considered by the investigator as related to AMG 176 treatment were reported in 4 subjects (40%); by preferred term, the most frequently reported events (occurring in >1 subject) were nausea (20%) and increased blood bilirubin (20%).

Rationale for Performing Clinical Studies with AMG 176

Apoptosis is well established as a survival mechanism used by many types of cancer cells (Fouad and Aanei, Am J Can Res 7:1016-1036 (2017); Hanahan and Weinberg, Vell 144:646-674 (2011)). Malignant transformation results in cellular stress from a variety of pro-apoptotic insults, including hypoxia and gain-of-function mutations in oncogenes, such that there is a strong selective advantage for tumors to evolve mechanisms that culminate in the evasion of apoptosis.

Apoptosis is regulated by a complex network of protein-protein interactions between the pro- and anti-apoptotic subgroups that form the BCL2 protein family (Czabotar et al, 2014; Strasser et al, 2011; Kozopas et al, 1993). Myeloid cell leukemia 1 is an anti-apoptotic member of this family and promotes cell survival. In contrast, pro-apoptotic family members such as the mitochondrial-pore-forming factors BAK, BAX, or the BH3-only protein family members, such as BIM and PUMA, are critical effectors for the induction of apoptosis. Upon the induction of apoptotic stimuli, pro-apoptotic BH3-only proteins bind MCL1 and other pro-survival BCL2 family members, disrupting interactions between MCL1 and the pro-apoptotic effector proteins, BAK and BAX. This disruption leads to activation and oligomerization of BAK and BAX; MOMP; release of cytochrome C; caspase activation; and cell death (Czabotar et al, 2014; Strasser et al, 2011). Myeloid cell leukemia 1 is expressed in a range of human and mouse tissues. In the mouse, for example, conditional gene-knockout studies have shown that MCL1 is important for the survival of a number of cell types including lymphocytes, hematopoietic stem cells, neutrophils, and cardiomyocytes (Thomas et al, 2013; Wang et al, 2013; Strasser et al, 2011).

Over-expression of MCL1 has been implicated in the development of a number of solid and hematopoietic human cancers (Ashkenazi et al 2017; Merino et al, 2017; Kotschy et al, 2016; Glaser et al, 2012), and in resistance to chemotherapy and to BCL2/BCL-XL inhibitors (Wertz et al, Nature 471:119-114 (2011); van Delft et al, Cancer Cell 10:389-399 (2006)). Focal amplification of the MCL1 gene has been observed in up to 10% of cancers derived from multiple tissue types, including lung and breast (Beroukhim et al. Nature 463:899-905 (2010)). These findings suggest that the inhibition of MCL1 represents a novel and compelling therapeutic strategy for the treatment of cancer.

AMG 176 is a small-molecule, potent, and selective inhibitor of protein-protein interactions between MCL1 and pro-apoptotic members of the BCL2 family that is being developed with the intention of treating patients with hematological malignancies, including multiple myeloma and AML. In vitro, AMG 176 resulted in a dose-dependent inhibition of the interaction between MCL1 and the pro-apoptotic effector protein, BAK, and treatment with AMG 176 led to rapid induction of apoptosis in hematological cancer cell lines. In vivo, treatment with AMG 176 significantly inhibited the growth of multiple myeloma and AML tumor xenograft models.

All human studies were performed following the guidelines of the appropriate regulatory agency.

Pharmaceutical Formulations

The compound of Formula I (AMG 176) used is an anhydrous crystalline material that is a white to light brown powder. It is formulated as a sterile concentrate solution for infusion. The concentrate solution is administered intravenously after dilution into an IV bag containing normal saline (0.9% sodium chloride (9 g/L)).

Dosage Form

AMG 176 may be synthesized using the procedures set forth in WO 2016/033486 and U.S. Pat. No. 9,562,061. AMG 176 was formulated as a sterile concentrate for solution for infusion at a concentration of 25 mg/mL in 10% w/w hydroxypropyl-β-cyclodextrin (HPβCD)(Cavitron™ W7 HP7 PHARMA high molar substitution grade (commercially available from Ashland Inc. (Covington, KY) and buffered with 100 mM glycine (commercially available from Sigma Aldrich (St. Louis, MO) and from EMD Millipore (Burlington, MA)) to pH 9. AMG 176 was thus supplied as a sterile, preservative-free solution for IV infusion in a single-use vial containing 10 mL of 25 mg/mL AMG 176. A single-use vial containing 14.4-mL of 25 mg/mL AMG 176 was also prepared and found useful.

The primary container closure system for the 10-mL concentrate solution was a 20 mL borosilicate glass vial with a 20 mm elastomeric stopper and an aluminum seal with flip-off dust cover. For the 14.4-mL concentrate solution, a 30R aluminosilicate glass vial with a 20 mm elastomeric stopper and an aluminum seal with flip-off dust cover was used.

The AMG 176 sterile concentrate solution vials were manufactured via a solution compounding and sterile fill process. First, the compounding vessel was charged with Water for Injection (WFI) by weight to approximately 70% to 75% of the total batch weight. Mixing was then initiated and the HPβCD was charged to the vessel and it was mixed until the cyclodextrin was dissolved. Sodium hydroxide was then added to the vessel and the resulting mixture was mixed until the NaOH was dissolved. The resulting mixture was then warmed to 45° C. AMG 176 was then added to the vessel while maintaining the temperature at 45° C., and the resulting mixture was mixed until the AMG 176 was dissolved. The resulting solution was cooled to 25° C. and glycine was then added to the vessel. The resulting mixture was mixed until all the glycine was dissolved. Hydrochloric acid (1 M) was incrementally added to the vessel while mixing until the pH of the solution was 9.1. The vessel was then charged with WFI, quantum sufficit (Q.S.), to approximately 95% of the total batch weight. The pH of the solution was measured and, if necessary, 1 M HCl was added until the target pH of 9.1 was achieved. WFI, Q.S., was then added to provide 100% of the total batch weight. The pH and concentration of AMG 176 was then determined. Using a polyethersulfone (PES) 0.2 μm filter, filtration of the bulk drug product was performed while transferring the contents from the compounding vessel to an appropriate hold vessel. Pre- and post-filtration integrity testing was performed on the filter unit. The hold vessel was closed at a temperature of less than 30° C. until initiation of sterile filtration and filling. The sample solution was then filtered through a single in-line PES 0.2 μM sterilization filter into a second sterile vessel prior to filling and filter integrity tests were performed before and after filtration. The filtered mixture was then used to fill vials to the target volume and the vials were then capped and sealed after checking the fill weight. The sealed vials were stored at or below 25° C. and protected from light. Visual inspections were then performed and vials were pulled for specification testing.

Adult patients with relapsed or refractory AML received intravenous AMG 176 (infused over a minimum of 2 hours) on days 1, 2, 8, 9, 15, and 16 of a 28-day cycle as part of a dose-escalation study. Escalating doses started at 60 $mg/m^2$. For dose levels ≥180 $mg/m^2$, a lead-in dose of 120 $mg/m^2$ was implemented during week 1. Primary objectives included the evaluation of safety, tolerability, and pharmacokinetics. The secondary objective was a preliminary evaluation of efficacy, assessed using ELN criteria. Exploratory endpoints included pharmacodynamic evaluation of MCL-1 inhibition in circulating AML blasts.

At the data cutoff date (May 17, 2019), 11 patients (median age [range]=74 [36-81] years) received AMG 176 (60 $mg/m^2$, n=5; 120 $mg/m^2$, n=5; 180 $mg/m^2$, n=1). Patients received a median (range) of 2 (1-5) prior lines of therapy, and 7 patients received prior venetoclax. Patients were treated with AMG 176 for a median (range) of 1 (1-6) cycles. Ten of the 11 patients discontinued treatment. The reasons for discontinuation were disease progression, n=5; adverse events, n=3; and patient request, n=2). Treatment-emergent adverse events (TEAEs) of any grade occurred in 10 (91%) patients, and grade ≥3 TEAEs occurred in 8 (73%) patients (Table 3). Common TEAEs of any grade (occurring in ≥3 patients) were peripheral edema (n=4, 36%) and nausea (n=4, 36%). Common grade ≥3 TEAEs (occurring in ≥2 patients) were anemia (n=2, 18%). Treatment-related AEs occurred in 5 (46%) patients; grade ≥3 treatment-related AEs occurred in 2 (18%) patients. No fatal adverse events were observed.

AMG 176 maximum plasma concentrations were observed close to the end of intravenous infusion as expected, and AMG 176 plasma exposures increased in a dose-related manner. Four out of the 11 patients had a postbaseline response assessment at data cutoff, and the best overall responses were complete remission with incomplete hematologic recovery (CRi; n=1, at the 60-$mg/m^2$ dose), partial remission (n=1, at the 60-$mg/m^2$ dose), and stable disease (n=2). In the patient achieving CRi, evidence of pharmacodynamic impact was observed through release of the proapoptotic protein Bax and activation of effector caspase 3 in peripheral blood AML blasts at 3 hours postinfusion. At the data cutoff date, the maximum tolerated dose of AMG 176 was not yet reached.

At the dose levels evaluated, AMG 176 administered as a monotherapy has an acceptable safety, tolerability, and pharmacokinetic profile. Preliminary evidence of on-target proapoptotic activity in vivo was observed, and clinical efficacy was observed in two patients to date. Further evaluation of the safety and efficacy of AMG 176 in patients with AML is ongoing.

TABLE 3

Adverse Events

| | Patients (N = 11) |
|---|---|
| All TEAEs, n (%) | 10 (90.9) |
| Grade ≥3 | 8 (72.7) |
| Serious | 8 (72.7) |
| Fatal | 0 |
| TEAEs occurring in ≥2 patients, n (%) | |
| Peripheral edema | 4 (36.4) |
| Nausea | 4 (36.4) |
| Increased blood bilirubin level | 2 (18.2) |
| Hypomagnesemia | 2 (18.2) |
| Anemia | 2 (18.2) |
| Hypokalemia | 2 (18.2) |
| Vomiting | 2 (18.2) |
| Grade ≥3 TEAEs occurring in ≥2 patients, n (%) | |
| Anemia | 2 (18.2) |

TEAE = treatment-emergent adverse event.

All publications, patents, and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the scope of the appended claims.

The invention claimed is:

1. A pharmaceutical formulation for intravenous administration, the formulation comprising:

a) a compound of Formula I or a salt thereof, wherein the compound of Formula I has the following structure:

I

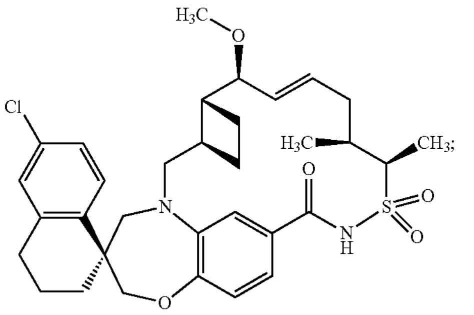

b) a cyclodextrin compound;

c) a buffer; and d) water, wherein, the concentration of the compound of Formula I or the salt thereof in the formulation ranges from 15 mg/mL to 30 mg/mL and the pH of the formulation ranges from 8.7 to 9.9;

wherein the buffer is glycine at a concentration ranging from 80 mM to 120 mM; and wherein the cyclodextrin compound is hydroxypropyl-β-cyclodextrin, and the amount of the cyclodextrin compound in the formulation ranges from 7.5 to 13 percent weight by weight.

2. The pharmaceutical formulation of claim 1, wherein the pH of the formulation is from 8.8 to 9.8.

3. The pharmaceutical formulation of claim 2, wherein the pH of the formulation ranges from 8.9 to 9.2.

4. The pharmaceutical formulation of claim 1, wherein the concentration of the compound of Formula I, or the salt thereof, in the formulation ranges from 20 to 30 mg/mL.

5. The pharmaceutical formulation of claim 4, wherein the concentration of the compound of Formula I, or the salt thereof, in the formulation ranges from 24 to 26 mg/mL.

6. The pharmaceutical formulation of claim 1, wherein the amount of the cyclodextrin compound in the formulation ranges from 9 to 11 percent weight by weight.

7. The pharmaceutical formulation of claim 1, wherein the formulation is buffered with glycine at a concentration ranging from 95 mM to 105 mM.

8. The pharmaceutical formulation of claim 1, wherein the volume of the formulation ranges from 5 mL to 25 mL.

9. The pharmaceutical formulation of claim 8, wherein the volume of the formulation ranges from 9 mL to 15 mL.

10. The pharmaceutical formulation of claim 1, wherein the formulation is an aqueous formulation comprising from 20 mg/mL to 30 mg/mL of the compound of Formula I and from 8 percent to 12 percent weight by weight hydroxypropyl-β-cyclodextrin and is buffered with 90 mM to 110 mM glycine to a pH of 8.8 to 9.2.

11. The pharmaceutical formulation of claim 1, wherein the formulation is an aqueous formulation comprising 25 mg/mL of the compound of Formula I and 10 percent weight by weight hydroxypropyl-β-cyclodextrin buffered with 100 mM glycine to a pH of 9.

12. The pharmaceutical formulation of claim 10, wherein the amount of the formulation ranges from 9 mL to 15 mL.

13. The pharmaceutical formulation of claim 10, wherein the formulation is contained within a vial.

14. The pharmaceutical formulation of claim 13, wherein the vial is a 20 mL borosilicate glass vial or a 20 mL aluminosilicate glass vial, wherein the vial is equipped with a stopper and an aluminum seal with a flip off cover.

15. An aqueous solution of a therapeutic agent, the solution comprising:

(a) a compound of Formula I or a salt thereof, wherein the compound of Formula I has the following structure:

I

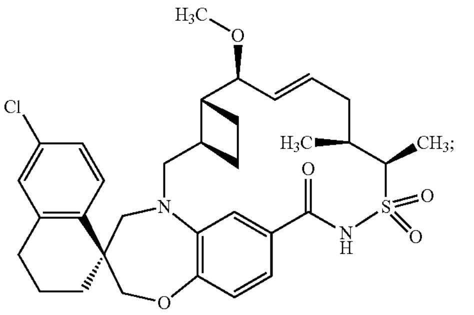

b) a cyclodextrin compound;

c) a buffer;

d) sodium chloride; and e) water, wherein, the amount of the compound of Formula I or the salt of the compound of Formula I in the solution ranges from 25 mg to 400 mg;

wherein the buffer is glycine at a concentration ranging from 80 mM to 120 mM; and wherein the cyclodextrin compound is hydroxypropyl-β-cyclodextrin, and the amount of the cyclodextrin compound in the formulation ranges from 7.5 to 13 percent weight by weight.

16. The aqueous solution of claim 15, wherein the amount of the compound of Formula I or the salt of the compound of Formula I in the solution ranges from 200 mg to 360 mg.

17. The aqueous solution of claim 15, wherein the solution is contained in an IV bag.

18. A method for making an aqueous solution suitable for intravenous infusion into a patient, the method comprising: combining the pharmaceutical formulation of claim 1 with a saline solution.

19. The method of claim 18, wherein the saline solution, prior to combining the pharmaceutical formulation with the saline solution, comprises sodium chloride in an amount ranging from 8 g/L to 10 g/L.

20. An aqueous solution of a therapeutic agent, the solution comprising: a compound of Formula I or a salt thereof, wherein the compound of Formula I has the following structure:

I

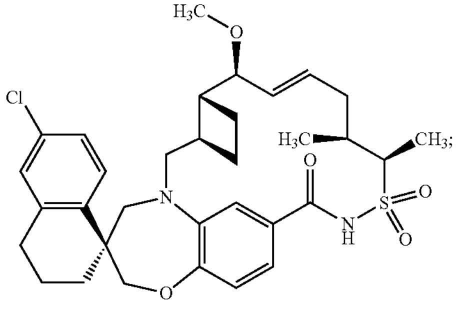

wherein, the compound of Formula I or the salt of the compound of Formula I is present in an amount ranging from 25 $mg/m^2$ to 960 $mg/m^2$;

wherein the aqueous solution further comprises a cyclodextrin compound, a buffer, and sodium chloride;

wherein the buffer is glycine at a concentration ranging from 80 mM to 120 mM; and wherein the cyclodextrin compound is hydroxypropyl-β-cyclodextrin and the amount of the cyclodextrin compound in the formulation ranges from 7.5 to 13 percent weight by weight.

21. The aqueous solution of claim 20, wherein the compound of Formula I or the salt of the compound of Formula I is present in an amount ranging from 25 $mg/m^2$ to 250 $mg/m^2$.

22. The aqueous solution of claim 20, wherein the compound of Formula I or the salt of the compound of Formula I is present in a dose ranging from 60 $mg/m^2$ to 180 $mg/m^2$.

* * * * *